US011534763B2

(12) United States Patent
Holden et al.

(10) Patent No.: US 11,534,763 B2
(45) Date of Patent: Dec. 27, 2022

(54) DROPLET INTERFACES IN ELECTRO-WETTING DEVICES

(71) Applicants: Oxford Nanopore Technologies PLC, Oxford (GB); Sharp Life Science (EU) Ltd, Oxfordshire (GB)

(72) Inventors: Matthew Holden, Oxford (GB); James White, Oxford (GB); Andrew John Heron, Oxford (GB); James Anthony Clarke, Oxford (GB); Jason Robert Hyde, Oxford (GB); Benjamin James Hadwen, Oxford (GB); Sally Anderson, Oxford (GB)

(73) Assignees: Oxford Nanopore Technologies PLC, Oxford (GB); Sharp Life Science EU (Ltd), Oxfordshire (GB)

( * ) Notice: Subject to any disclaimer, the term of this patent is extended or adjusted under 35 U.S.C. 154(b) by 18 days.

(21) Appl. No.: 16/955,762

(22) PCT Filed: Dec. 21, 2018

(86) PCT No.: PCT/US2018/067219
§ 371 (c)(1),
(2) Date: Jun. 18, 2020

(87) PCT Pub. No.: WO2019/126715
PCT Pub. Date: Jun. 27, 2019

(65) Prior Publication Data
US 2021/0008557 A1    Jan. 14, 2021

(30) Foreign Application Priority Data

Dec. 21, 2017  (GB) ...................................... 1721649

(51) Int. Cl.
C12Q 1/68         (2018.01)
B01L 3/00         (2006.01)
(Continued)

(52) U.S. Cl.
CPC ...... *B01L 3/502792* (2013.01); *C12Q 1/6869* (2013.01); *G01N 33/48721* (2013.01);
(Continued)

(58) Field of Classification Search
CPC ........................................................ C12Q 1/68
(Continued)

(56) References Cited

U.S. PATENT DOCUMENTS 6,565,727 B1    5/2003   Shenderov
6,911,132 B2    6/2005   Pamula et al.
(Continued)

FOREIGN PATENT DOCUMENTS

CN    102671723 A    9/2012
CN    107107020 A    8/2017
(Continued)

OTHER PUBLICATIONS

International Search Report and Written Opinion for Application No. PCT/US2018/067219, dated May 27, 2019.
(Continued)

*Primary Examiner* — Aaron A Priest
(74) *Attorney, Agent, or Firm* — Wolf, Greenfield & Sacks, P.C.

(57) ABSTRACT

Droplet interfaces are formed between droplets in an electro-wetting device comprising an array of actuation electrodes. Actuation signals are applied to selected actuation electrodes to place the droplets into an energised state in which the shape of the droplets is modified compared to a shape of the droplets in a lower energy state and to bring the two droplets into proximity. The actuation signals are then changed to lower the energy of the droplets into the lower energy state so that the droplets relax into the gap and the two droplets contact each other thereby forming a droplet interface. The use of sensing electrodes in the device permit electrical
(Continued)

current measurements across the droplet interface. The sensing electrodes can be used for either (i) applying a reference signal during droplet actuation or (ii) recording electrical current measurements.

30 Claims, 8 Drawing Sheets

(51) Int. Cl.
*C12Q 1/6869* (2018.01)
*G01N 33/487* (2006.01)
(52) U.S. Cl.
CPC . *B01L 2300/0645* (2013.01); *B01L 2300/165* (2013.01); *B01L 2400/0427* (2013.01)
(58) Field of Classification Search
USPC .......................................................... 435/6.1
See application file for complete search history.

(56) References Cited

U.S. PATENT DOCUMENTS

| | | | |
|---|---|---|---|
| 6,916,488 B1 | 7/2005 | Meier et al. | |
| 7,163,612 B2 | 1/2007 | Sterling et al. | |
| 8,547,111 B2 | 10/2013 | Hadwen et al. | |
| 8,653,832 B2 | 2/2014 | Hadwen et al. | |
| 2010/0194408 A1 | 8/2010 | Sturmer et al. | |
| 2011/0220505 A1 | 9/2011 | Wang et al. | |
| 2011/0247934 A1 | 10/2011 | Wang et al. | |
| 2012/0007608 A1* | 1/2012 | Hadwen ................. | G09G 3/348 324/649 |
| 2014/0216932 A1* | 8/2014 | Srinivasan ........ | B01L 3/502792 204/600 |
| 2014/0262783 A1 | 9/2014 | Chang et al. | |
| 2016/0108433 A1* | 4/2016 | Fair ....................... | C12M 35/02 435/173.6 |
| 2016/0305906 A1 | 10/2016 | Amos et al. | |

FOREIGN PATENT DOCUMENTS

| | | |
|---|---|---|
| CN | 107249729 A | 10/2017 |
| EP | 2756885 A2 | 7/2014 |
| GB | 2533952 A | 7/2016 |
| WO | WO 2008/012552 A1 | 1/2008 |
| WO | WO 2008/147568 A1 | 12/2008 |
| WO | WO 2009/024775 A1 | 2/2009 |
| WO | WO 2010/086603 A1 | 8/2010 |
| WO | WO 2011/067559 A1 | 6/2011 |
| WO | WO 2012/107778 A2 | 8/2012 |
| WO | WO 2012/164270 A1 | 12/2012 |
| WO | WO 2013/041878 A1 | 3/2013 |
| WO | WO 2013/083983 A1 | 6/2013 |
| WO | WO 2013/121224 A1 | 8/2013 |
| WO | WO 2013/153359 A1 | 10/2013 |
| WO | WO 2014/064443 A2 | 5/2014 |
| WO | WO 2015/140535 A1 | 9/2015 |
| WO | WO 2015/150786 A1 | 10/2015 |
| WO | WO 2016/034591 A2 | 3/2016 |
| WO | WO 2017/004463 A1 | 1/2017 |
| WO | WO 2017/004504 A1 | 1/2017 |
| WO | WO 2017/038064 A1 | 3/2017 |
| WO | WO 2017/149316 A1 | 9/2017 |
| WO | WO 2017/149317 A1 | 9/2017 |
| WO | WO 2017/149318 A1 | 9/2017 |
| WO | WO 2018/100370 A1 | 6/2018 |

OTHER PUBLICATIONS

International Preliminary Report on Patentability for Application No. PCT/US2018/067219, dated Jul. 2, 2020.
Aghdaei et al., Formation of artificial lipid bilayers using droplet dielectrophoresis. Lab Chip. 2008;8(10):1617-1620. doi:10.1039/b807374k.
Altschul et al., Basic local alignment search tool. J Mol Biol. 1990;215(3):403-410. doi:10.1016/S0022-2836(05)80360-2.
Altschul, A protein alignment scoring system sensitive at all evolutionary distances. J Mol Evol. 1993;36(3):290-300. doi:10.1007/BF00160485.
Boza et al., DeepNano: Deep recurrent neural networks for base calling in MinION nanopore reads. PLoS One. 2017;12(6):e0178751. Published Jun. 5, 2017. doi:10.1371/journal.pone.0178751.
Choi et al., Integration of field effect transistor-based biosensors with a digital microfluidic device for a lab-on-a-chip application. Lab Chip. 2012;12(8):1533-1539. doi:10.1039/c2lc21203j.
Devereux et al., A comprehensive set of sequence analysis programs for the VAX. Nucleic Acids Res. 1984;12(1 Pt 1):387-395. doi:10.1093/nar/12.1part1.387.
Ghazian et al., Electric-field-induced oscillations of water droplets deposited on insulating surfaces. Journal of Electrostatics Jun. 2013;71(3):489-495. doi: 10.1016/j.elstat.2012.11.012.
Gilboa et al., Optical sensing and analyte manipulation in solid-state nanopores. Analyst. 2015;140(14):4733-4747. doi:10.1039/c4an02388a.
Holden et al., Functional bionetworks from nanoliter water droplets. J Am Chem Soc. 2007;129(27):8650-8655. doi:10.1021/ja072292a.
Issadore, Hybrid integrated circuit/microfluidic chips for the control of living cells and ultra-small biomimetic containers. Dissertation. Jan. 1, 2009, ISBN: 978-1-109-25494-5. Retrieved from the Internet https://meso.seas.harvard.edu/theses/issadore.pdf. 161 pages.
Langecker et al., Synthetic lipid membrane channels formed by designed DNA nanostructures. Science. 2012;338(6109):932-936. doi:10.1126/science.1225624.
Leptihn et al., Constructing droplet interface bilayers from the contact of aqueous droplets in oil. Nat Protoc. 2013;8(6):1048-1057. doi:10.1038/nprot.2013.061.
Lieberman et al., Processive replication of single DNA molecules in a nanopore catalyzed by phi29 DNA polymerase. J Am Chem Soc. 2010;132(50):17961-17972. doi:10.1021/ja1087612.
Luan et al., Base-by-base ratcheting of single stranded DNA through a solid-state nanopore. Phys Rev Lett. 2010;104(23):238103. doi:10.1103/PhysRevLett.104.238103.
Martel et al., Handling of artificial membranes using electrowetting-actuated droplets on a microfluidic device combined with integrated pA-measurements. Biomicrofluidics. 2012;6(1):12813-128137. doi:10.1063/1.3665719.
Montal et al., Formation of Bimolecular Membranes from Lipid Monolayers and a Study of Their Electrical Properties. Proc Natl Acad Sci U S A. Dec. 1972; 69(12): 3561-3566. doi:10.1073/pnas.69.12.3561.
Nardin et al., Polymerized ABA Triblock Copolymer Vesicles. Langmuir Nov. 20, 2000;16(3):1035-1041. doi: 10.1021/la990951u.
Poulos et al., Electrowetting on dielectric-based microfluidics for integrated lipid bilayer formation and measurement. App Phys Lett. Jul. 8, 2009;95:013706. 4 pages.
Soni et al., Synchronous optical and electrical detection of biomolecules traversing through solid-state nanopores. Rev Sci Instrum. 2010;81(1):014301. doi:10.1063/1.3277116.
Yi et al., Characterization of electro wetting actuation on addressable single-side coplanar elctrodes. J Micromech Microeng. Aug. 25, 2006;16:2053-2059.
Invitation to Pay Additional Fees for Application No. PCT/US2018/067219, dated Mar. 26, 2019.

* cited by examiner

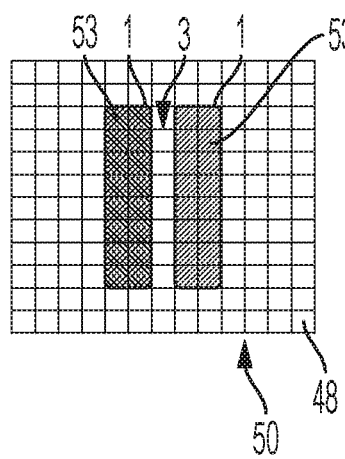 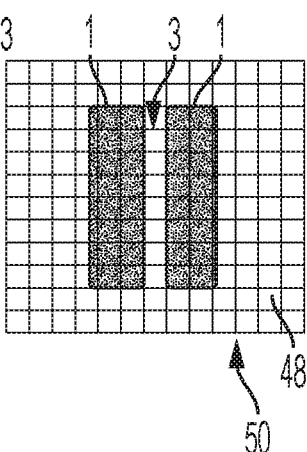 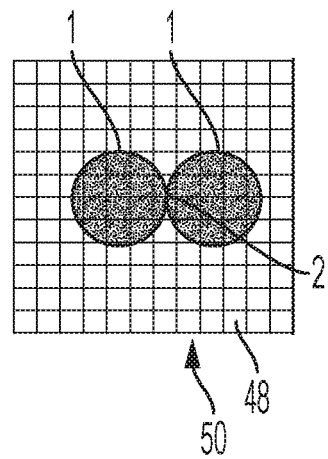
FIG. 10          FIG. 11          FIG. 12
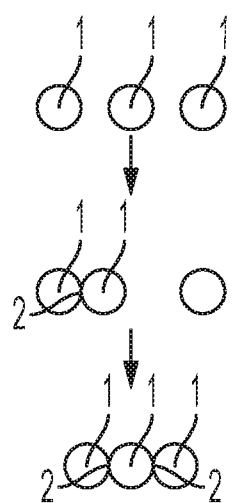      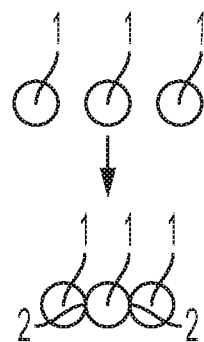
FIG. 13          FIG. 14
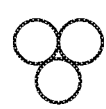      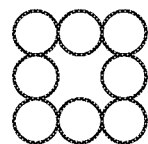
FIG. 15          FIG. 16

DROPLET INTERFACES IN ELECTRO-WETTING DEVICES

In some aspects, the present invention relates to electro-wetting devices and their use to form droplet interfaces between droplets of liquid in a fluid medium. In some aspects, the present invention relates to electro-wetting devices and their use is making measurements on droplet interfaces formed using electro-wetting.

Electro-wetting devices, for example electro-wetting on dielectric (EWOD) devices, are known for manipulating droplets of liquid in a fluid medium.

Considering this in more detail, electro-wetting on dielectric is a well-known technique for manipulating droplets of fluid by the application of an electric field, for example as disclosed in US2016/0305906. Example configurations and operation of EWOD devices are described in the following documents. U.S. Pat. No. 6,911,132 discloses a two-dimensional EWOD array to control the position and movement of droplets in two dimensions. U.S. Pat. No. 6,565,727 discloses methods for other droplet operations including the splitting and merging of droplets, and the mixing together of droplets of different materials. U.S. Pat. No. 7,163,612 describes how an active matrix (AM) arrangement based on thin film electronics including thin-film transistors (TFT) may be used to control the addressing of voltage pulses to an EWOD device, using circuit arrangements similar to those employed in AM display technologies. Devices of this general type may be referred to as AM-EWOD devices.

It has been proposed to use EWOD devices to manipulate such droplets to form droplet interfaces between droplets, for example comprising a membrane of amphipathic molecules. That provides a potentially useful system for studying the droplet interfaces themselves, and also processes occurring at the droplet interfaces. In one example having particular interest, such processes may involve insertion of a transmembrane pore, and subsequent measurement of properties such as ion current flow that may be dependent on interaction of an analyte with such a transmembrane pore.

Membranes of amphipathic molecules, for example artificial planar lipid bilayers may serve as simplified models of biological membranes and are widely used for the study of various processes, including the characterisation of transmembrane pores, such as transmembrane protein pores, for example ion-channels. Ion-channels are a diverse group of transmembrane protein pores that in biology selectively control the movement of specific ions across cell membranes, establishing voltage and electrochemical gradients that are fundamental to a wide variety of biological processes.

Single-channel recording (SCR) of individual protein pores is a powerful means of studying channel protein function. Single-channel recording measures changes in ion-current through single protein channels, and can examine voltage dependence, gating behaviour, ligand binding affinity, and ion selectivity at the single-molecule level. Various methods may be employed to form lipid bilayers such as disclosed by Montal, M. & Mueller, P. 1972. Proceedings of the National Academy of Sciences of the United States of America 69, 3561-3566). Although widely used, planar lipid bilayers are difficult to prepare, and their short lifetime prohibits their use in many situations.

Thus other membranes of amphipathic molecules have been proposed. Alternatives to planar lipid bilayers are disclosed, for example, WO-2008/012552 which discloses a method of forming bilayers of amphipathic molecules uses droplets of aqueous solution in a hydrophobic medium such as oil.

Arrays of individual suspended membranes of amphipathic molecules containing respective ion channel protein pores or nanopores may be provided, for example disclosed in WO-2014/064443. Ion current between two aqueous solutions provided at either side of the amphipathic membrane may be measured in order to characterise an analyte such as polynucleotide and commercial devices such as the MinION™ comprising a nanopore array that is able to determine a polynucleotide sequence are sold by Oxford Nanopore Technologies Ltd.

Droplet interfaces between droplets in contact with one another are therefore an alternative way of forming membranes of amphipathic molecules. Such a membrane formed by a bilayer of amphipathic molecules may be referred to as a droplet interface bilayer (DIB). Multiple membranes can be formed at the interface between multiple pairs of droplets. Techniques for forming DIBs are disclosed for example in Leptihn et al, Nature Protocols 8, 1048-1057 (2013) and DIBs may be used for the study of transmembrane pores inserted therein. For example, Martel et al., Biomicrofluidics 6, 012813 (2012) discloses a microfluidic device for forming droplet interface bilayers into which a protein channel was inserted. Gold microwires were deposited onto the substrate including the actuation electrodes upon which Ag/AgCl pads were provided in order to make electrical contact with each droplet in order to carry out measurements of ion current flow through the membrane channel.

The first aspect of the present invention is concerned with methods and devices for forming a droplet interface in an electro-wetting device.

According to a first aspect of the present invention, there is provided a method of forming a droplet interface in an electro-wetting device, the electro-wetting device comprising: an array of actuation electrodes; an insulator layer covering the actuation electrodes and having an outermost hydrophobic surface; disposed on the hydrophobic surface, a fluid medium and two droplets comprising liquid in the fluid medium, one of the liquid and the fluid medium being polar, and the other of the liquid and the fluid medium being apolar, whereby the actuation electrodes are capable of electro-wetting the droplets when actuation signals are applied thereto, the method comprising: applying actuation signals to selected actuation electrodes to place one or both of the two droplets in an energised state in which the shape of said one or both droplets is modified compared to when in a lower energy state and to bring the two droplets into proximity with a gap therebetween, the gap being chosen such that the two droplets do not contact each other when one or both are in the energised state and contact each other to form a droplet interface when in the lower energy state; and changing the actuation signals applied to the actuation electrodes to lower the energy of said one or both droplets into the lower energy state so that said one or both droplets relax into the gap and the two droplets contact each other thereby forming a droplet interface.

This method is applied to an electro-wetting device that comprises an array of actuation electrodes and an insulator layer covering the actuation electrodes and having an outermost hydrophobic surface. In such an electro-wetting device, a fluid medium and two droplets comprising liquid in the fluid medium may be disposed on the hydrophobic surface. The actuation electrodes are capable of electro-wetting the droplets when actuation signals are applied thereto, thereby allowing manipulation of the droplets by selection of the actuation signals.

The method provides a reliable technique for forming a droplet interface between two droplets. With the present method the actuation signals are applied to the actuation electrodes in two phases. In the initial phase, the applied actuation signals have a pattern selected to place one or both of the two droplets in an energised states. As a result, the shape of one or both droplets is modified compared to when in a lower energy state. In such an energised state, the two droplets are brought into proximity with a gap therebetween. The gap is chosen such that the two droplets do not contact each other when one or both are in the energised state and contact each other to form a droplet interface when in the lower energy state.

In a subsequent phase, the applied actuation signals are changed to lower the energy of said one or both droplets into a lower energy state. As a result, one or both droplets relax into the gap and the two droplets contact each other. A droplet interface is thereby formed between the two droplets. Thus, movement of a surface of the one or both droplets is caused by relaxation of the energised state, which is a passive process.

This process improves the reliability of formation of the droplet interface, compared to attempting to bring two droplets into contact directly by applying actuation signals that move the entire droplets towards one another. While such methods might be possible in principle, the droplets have a tendency to fuse (i.e. merge) and it is difficult to maintain the interface between the droplets.

While the method may be applied by placing a single one of the two droplets in an energised state, preferably both droplets are placed in the energised state. As a result, the surfaces of both droplets relax into the gap and contact each other to form the droplet interface. In this manner, relaxation of both droplets is used to form the droplet interface, which further increases the reliability of formation.

In the energised state of the one or both droplets, any shape of the droplets may be selected that allows the desired relaxation of the surface to form the droplet interface. While various shapes are possible, advantageously the shape of the droplet in the energised state as viewed in the plane of the electro-wetting device is elongate. Similarly, the shape of the contact line of the droplet in the energised state is elongate. In that case, the gap between droplets may extend along a major length of the elongate shape, so that on relaxation, a surface of the droplet extending along the major length may move into the gap to contact the other droplet.

Where an elongate shape is used, the shape of the droplet in the energised state may have an aspect ratio of at least 2:1, preferably at least 4:1 or at least 8:1. In general, increasing the aspect ratio increases the degree of movement of the surface of the at least one droplet, which assists bringing the droplets into contact.

During the step of applying actuation signals to the actuation electrodes, the two droplets may be brought into proximity with the centroids of the two droplets, separated by a distance less than the combined radii of the droplets, along a line between the two centroids in the lower energy state of the droplets.

The method may be applied with advantage to an electro-wetting device wherein the area enclosed by the contact line of the droplets in the lower energy state covers at least two actuation electrodes, preferably at least 5 actuation electrodes, at least 10 actuation electrodes or at least 20 actuation electrodes. In general, in the design of the electro-wetting device, the more actuation electrodes a droplet covers the better the resolution of the control of the shape in the energised state of the droplet. That in turn allows the degree of movement of the surface of the at least one droplet to be increased, which assists bringing the droplets into contact.

The actuation signals that are selected to energise the one or more droplets may be alternating (AC) actuation voltage signals. In general, the use of AC actuation signals in an electro-wetting device is known to be advantageous for manipulating droplets. In that case, preferably, the step of changing the actuation signals applied to the selected actuation electrodes may comprise applying DC potentials or floating potentials to the selected actuation electrodes in place of the AC actuation signals. This improves the reliability of formation of the droplet interfaces, because the DC potentials or floating potentials are less likely to rupture the droplet interface than if AC actuation signals were maintained.

The method may be applied to an electro-wetting device wherein the insulator layer comprises a layer of electrically insulating material coated by a hydrophobic material that forms said hydrophobic surface.

The method may be applied to an electro-wetting device that further comprises a second substrate facing the hydrophobic surface of the insulator layer, wherein the second substrate is coated by a hydrophobic material forming a further hydrophobic surface facing the hydrophobic surface of the insulator layer. In this case, the droplets may be disposed on the further hydrophobic surface of the hydrophobic layer as well as the hydrophobic surface of the insulator layer. In this manner, the droplets are sandwiched between the two substrates, which constrains the shape of the droplets. This improves the degree of control of the shape of the droplets between the energised state and lower energy state, which in turn improves the reliability of the formation of droplet interfaces.

Furthermore, the second substrate may support sensor electrodes that make an electrical connection with the droplets between which a droplet interface is formed.

The method may be applied to an electro-wetting device that further comprises an active matrix arrangement connected to the actuation electrodes.

The method may be applied to form only a single droplet interface between two droplets, but equally the method may be applied with one or more further droplets disposed on the hydrophobic surface, and the steps of applying and changing actuation signals to the actuation electrodes may be performed to form plural droplet interfaces between plural pairs of droplets.

After formation of a droplet interface, electrical measurements may be taken between the droplets across the droplet interface. For example, the electrical measurements may be measurements of ion flow between droplets through a transmembrane pore and/or may be taken while applying a potential difference between the droplets.

Further according to the first aspect of the present invention, there is provided an electro-wetting device for forming a droplet interface which implements a similar method to that described above.

The second aspect of the present invention is concerned with making electrical connections to respective droplets in a system of droplets formed in an electro-wetting device and having one or more droplet interfaces between droplets. Such electrical connections may have the purpose of sensing a property of the droplets, such as the size or location of a droplet when performing various droplet operations in the electro-wetting device, or the purpose of taking measurements across a droplet interface.

US-2010/0,194,408 discloses a method, circuit and apparatus for detecting capacitance on a droplet actuator inter alia for determining the presence, partial presence or absence of a droplet at an actuation electrode. U.S. Pat. No. 8,653,832 describes how an impedance (or capacitance) sensing function can be incorporated into the array element circuit of each array element of an AM-EWOD device, wherein the impedance sensor circuit may be used for determining the presence and size of droplets present at each electrode in the array. However, these approaches are limited by the need to obtain signals from the same electrodes to which the actuation signals are applied.

Martel et al., Biomicrofluidics 6, 012813 (2012) discloses a microfluidic device for forming droplet interface bilayers into which a protein channel was inserted, wherein gold microwires were deposited onto the substrate including the actuation electrodes upon which Ag/AgCl pads were provided in order to make electrical contact with each droplet in order to carry out measurements of ion current flowing through the membrane channel. However, this construction is inconvenient and difficult to manufacture, as well as limiting the reliability of taking measurements and limiting the scalability of the technique.

According to a second aspect of the present invention, there is provided an electro-wetting device for taking measurements across a droplet interface, the electro-wetting device comprising: a first substrate supporting an array of actuation electrodes; an insulator layer covering the actuation electrodes and having a hydrophobic surface, a second substrate facing the hydrophobic surface of the insulator layer and supporting at least one set of at least two sensor electrodes, the electro-wetting device being arranged to receive a fluid medium and droplets comprising liquid in the fluid medium disposed on the hydrophobic surface, the actuation electrodes being configured to receive actuation signals for electro-wetting received droplets in order to form at least one system of droplets having one or more droplet interfaces between droplets, and the sensor electrodes of each set being configured to make electrical connections to respective droplets in the at least one system of droplets.

Thus, in the electro-wetting device, sensor electrodes are provided on a second substrate facing the facing the hydrophobic surface of the insulator layer that covers the actuation electrodes. Such sensor electrodes are arranged in at least one set of at least two sensor electrodes, and the sensor electrodes of each set are configured to make electrical connections to respective droplets in a system of droplets. This provides a convenient and reliable way to make electrical connections to the droplets.

The second substrate may be coated by a hydrophobic material forming a further hydrophobic surface facing the hydrophobic surface of the insulator layer. In that case, the electro-wetting device may be arranged to receive the fluid medium and the droplets disposed on the further hydrophobic surface of the hydrophobic layer as well as the hydrophobic surface of the insulator layer. In this manner, the droplets are sandwiched between the two substrates, which constrains the shape of the droplets. This improves the degree of control of the droplets by actuation signals applied to the actuation electrodes.

Where second substrate is coated by a hydrophobic material, then the hydrophobic material coating the second substrate may have apertures exposing at least part of the sensor electrodes. This improves the electrical connection between the sensor electrodes and the droplets.

The second substrate further supports at least one further electrode, for example for receiving a reference signal while actuation signals are applied to the actuation electrodes for manipulating the droplets.

The sensor electrodes and the further electrodes, where provided, may be deposited on a surface of the second substrate facing the first substrate. In that case, the further electrodes, where provided, may extend around the sensor electrodes.

The electro-wetting device may further comprise a control system that is connected to the actuation electrodes and is configured to apply actuation signals to the actuation electrodes for manipulating received droplets.

The control system may be configured, while applying actuation signals to the actuation electrodes, to apply a reference signal to the sensor electrodes and/or to the further electrodes, where provided.

The control system may be configured to apply actuation signals to the actuation electrodes selected to form a droplet interface at the interface between two droplets.

The electro-wetting device may further comprise a sensor system connected to the sensor electrodes and configured to take electrical measurements, for example including impedance measurements, between sensor electrodes that are electrically connected to respective droplets forming a droplet interface therebetween. Such electrical measurements may be taken across a droplet interface between two droplets in a system of droplets.

The sensor system may be configured to take electrical measurements between respective sensor electrodes that make contact between respective droplets across a droplet interface comprising a membrane of amphipathic molecules having a transmembrane pore inserted therein, for example measurements of ion flow between droplets through a transmembrane pore and/or electrical measurements that are dependent on an analyte that interacts with the transmembrane pore.

The sensor system may further comprise an analysis system configured to process the electrical measurements to analyse an analyte that interacts with the transmembrane pore. For example, where the analyte is a polymer comprising polymer units, the analysis system may be configured to process the electrical measurements to derive estimated identities of the polymer units of the polymer.

The third aspect of the present invention is concerned with use of an electro-wetting device to perform experiments on droplet interfaces.

According to a third aspect of the present invention, there is provided an apparatus for performing experiments on droplet interfaces, the apparatus comprising: an electro-wetting device comprising an array of actuation electrodes and an insulator layer covering the actuation electrodes and having an outermost hydrophobic surface, the electro-wetting device being arranged to receive a fluid medium and droplets comprising liquid in the fluid medium disposed on the hydrophobic surface, a control system configured to apply actuation signals to the actuation electrodes selected to manipulate received droplets and to form at least one system of droplets having one or more droplet interfaces between the droplets; and a sensor system configured to take electrical measurements between droplets in a formed system across droplet interfaces.

Such an apparatus is suitable for performing experiments on droplet interfaces.

The apparatus includes an electro-wetting device in which droplet interfaces may be formed. The electro-wetting device comprises an array of actuation electrodes and an insulator layer covering the actuation electrodes and having an outermost hydrophobic surface. The electro-wetting device can receive a fluid medium and droplets comprising liquid in the fluid medium disposed on the hydrophobic surface The apparatus further includes a control system configured to apply actuation signals to the actuation electrodes selected to manipulate received droplets and to form at least one system of droplets having one or more droplet interfaces between the droplets. Therefore, use of the control system allows droplet interfaces to be formed in the electro-wetting device.

The apparatus further includes a sensor system configured to take electrical measurements between droplets in a formed system across droplet interfaces, thereby allowing experiments to be performed on the formed droplet interfaces.

After formation of a droplet interface, various types of electrical measurements may be taken between the droplets across the droplet interface. For example, the electrical measurements may be measurements of ion flow between droplets through a transmembrane pore and/or may be taken while applying a potential difference between the droplets.

The sensor system may further comprise an analysis system configured to process the electrical measurements to analyse an analyte that interacts with the transmembrane pore. For example, where the analyte is a polymer comprising polymer units, the analysis system may be configured to process the electrical measurements to derive estimated identities of the polymer units of the polymer.

Advantageously, the control system may be arranged to modify the at least one formed system of droplets in response to the electrical measurements taken by the sensor system. The ability of the apparatus to modify the formed system of droplets based on feedback from the sensor system provides significant advantages, because it allows the apparatus to perform experiments on droplet interfaces in an adaptive manner.

The outputs of the sensor system to which the control system responds may include the electrical measurements themselves. This provides a first type of control of the experiments being performed based on the electrical properties being measured. As the electrical properties are fundamental to the relevant processes such as formation of droplet interfaces and reactions occurring there, this first type of control allows those processes to be considered and adaptively modified.

Alternatively, where the sensor system comprises an analysis system configured to process the electrical measurements, and said outputs of the sensor system include outputs of the analysis system. This provides a second type of control of the experiments being performed based on the analysis. As such analysis allows higher level information to be obtained, for example concerning analyte being analysed, this second type of control provides powerful experimental adaption based on the results of the analysis.

The types of control which may be performed are extensive, thereby providing a powerful experimental apparatus. Some non-limitative examples are as follows.

The formed system of droplets may be modified by separating a droplet interface in the system.

The formed system of droplets may be modified by moving a new droplet into contact with a current droplet in the system of droplets and forming a droplet interface between the new droplet and the current droplet.

The formed system of droplets may be modified by moving a new droplet into contact with a current droplet in the system of droplets and fusing the new droplet and the current droplet. In that case, it may be that the new droplet does not comprise amphipathic molecules at the interface between the liquid of the droplet and the fluid medium.

Advantageously, the control system may be arranged to apply actuation signals to the actuation electrodes selected to form plural systems of droplets in parallel. This allows the apparatus to perform experiments on the plural systems in parallel with each other, thereby increasing the experimental throughput of the apparatus.

The apparatus may further include a droplet preparation system configured to form droplets disposed on the hydrophobic surface of the electro-wetting device in the fluid medium. In this case, the control system may be configured to control the droplet preparation system to form the droplets. This increases the experimental power of the apparatus as it allows droplets containing appropriate reagents to be formed for experimental purposes.

The first to third aspects of the present invention may be implemented together, for example in the same device or apparatus. Accordingly, the preferred features of the first to third aspects of the present invention, some of which are defined in the dependent claims below, may be combined in any combination.

To allow better understanding, embodiments of the present invention will now be described by way of non-limitative example with reference to the accompanying drawings, in which:

FIGS. 8 to 12 are plan views of a pair of droplets on an array of actuation electrodes in the AM-EWOD device during successive stages of a method of forming a droplet interface between the droplets;

FIGS. 13 and 14 are plan views of respective ways of forming two systems of three droplets;

FIGS. 15 and 16 are plan views of respective systems of droplets.

OVERALL APPARATUS

Figure 1:
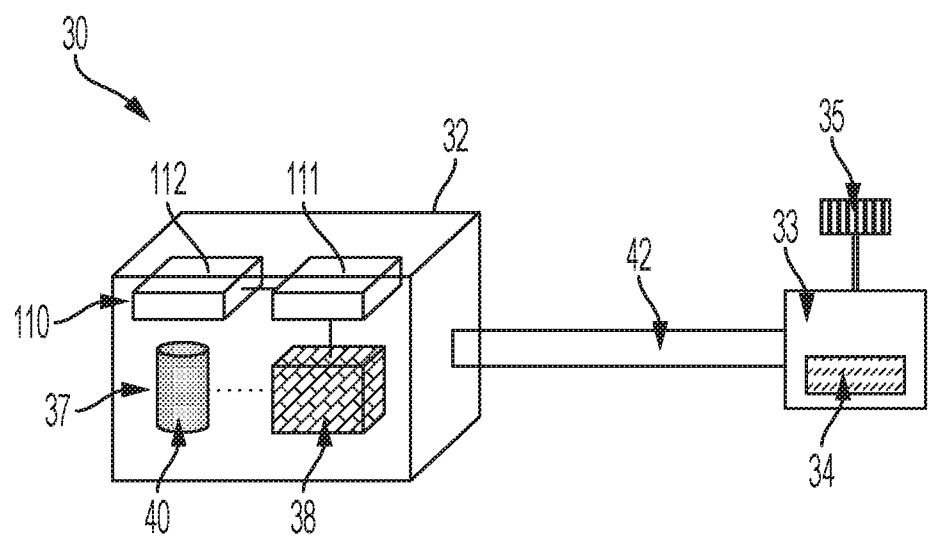
FIG. 1 is a schematic view of an apparatus including an AM-EWOD device.
Figure 2:
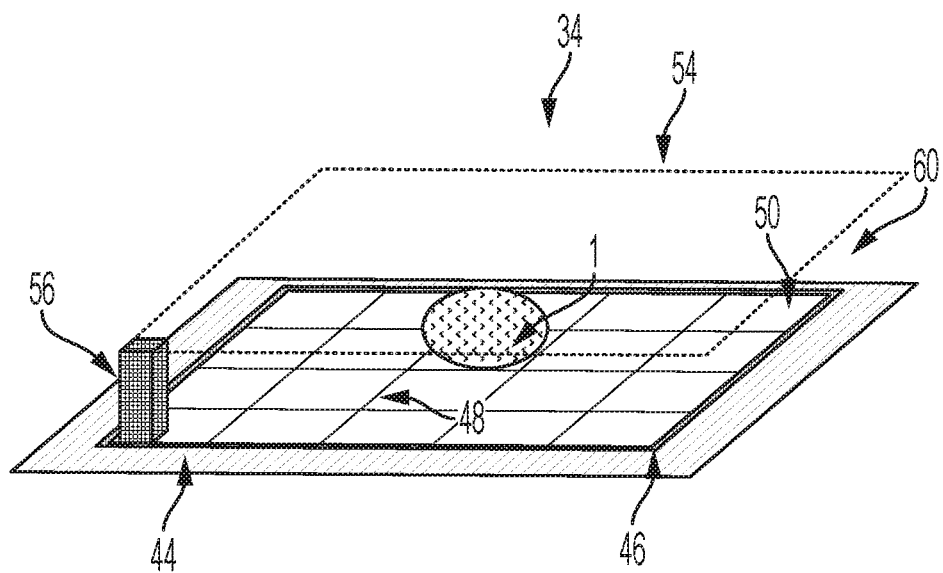
FIG. 2 is a schematic perspective view of the AM-EWOD device.

FIG. 1 illustrates an apparatus 30 for forming droplet interfaces and for performing experiments thereon. The apparatus 30 includes a reader 32 and a cartridge 33 that may be inserted into the reader 32. The cartridge 33 contains an AM-EWOD device 34 which is an example of an electro-wetting device. The AM-EWOD device 34 is shown in FIG. 2 and described further below.

The reader 32 and cartridge 33 may be electrically connected together while in use, for example by a cable of connecting wires 42, although various other methods (e.g. wireless connection) of providing electrical communication may be used.

The reader 32 also comprises a droplet preparation system 35 configured to form droplets 1 comprising liquid in a fluid medium 60 in the AM-EWOD device 34 when the cartridge 33 is inserted. Suitable material properties for the droplets 1 and the fluid medium 60 are discussed below. The droplet preparation system 35 may also be able to carry sample preparations to prepare an analyte to be measured, alternatively sample preparation may be carried out in the AM-EWOD device 34. The samples may be compartmentalised for a library preparation or for sequencing.

The droplet preparation system 35 may comprise fluid input ports that perform the function of inputting liquid into the AM-EWOD device 34 from one or more reservoirs and thereby generating droplets within AM-EWOD device 34. The droplet preparation system 35 may be formed by conventional fluidics elements, for example controlling flow of liquid by electro-wetting. The droplet preparation system 35 desirably has the ability to accurately control the volumes of created droplets 1, typically accurate to 2-3%. Typically, the droplets may have respective volumes between 1 nL and 10 µL.

The apparatus 30 further includes a control system 37 provided in the reader 32. In this example, the control system 37 includes control electronics 38 and a storage device 40 that may store any application software any data associated with the system. The control electronics 38 may include suitable circuitry and/or processing devices that are configured to carry out various control operations relating to control of the AM-EWOD device 34, such as a CPU, microcontroller or microprocessor.

Among their functions, to implement the features of the present invention, the control electronics 38 may comprise a part of the overall control system 37 that may execute program code embodied as a control application within the storage device 40. The storage device 40 may be configured as a non-transitory computer readable medium, such as random access memory (RAM), a read-only memory (ROM), an erasable programmable read-only memory (EPROM or Flash memory), or any other suitable medium. Also, while the code may be executed by control electronics 38 in accordance with an exemplary embodiment, such control system functionality could also be carried out via dedicated hardware, firmware, software, or combinations thereof.

As described in more detail below, the control system 37 is configured to perform control of various elements of the apparatus 1, including control of the droplet preparation system 35, to form the droplets 1 and control of the application of actuation signals for manipulating droplets. In particular, the control system 37 is configured to form one or more systems of two or more droplets 1. Within the or each system of droplets 1, one or more droplet interfaces are formed between respective pairs of droplets 1. The control system 37 may also provide a graphical user interface (GUI) to a user which provides for the user to input of program commands such as droplet operations (e.g. move a droplet), assay operations (e.g. perform an assay), and for displaying the results of such operations to the user.

Electro-Wetting Device

Figure 3:
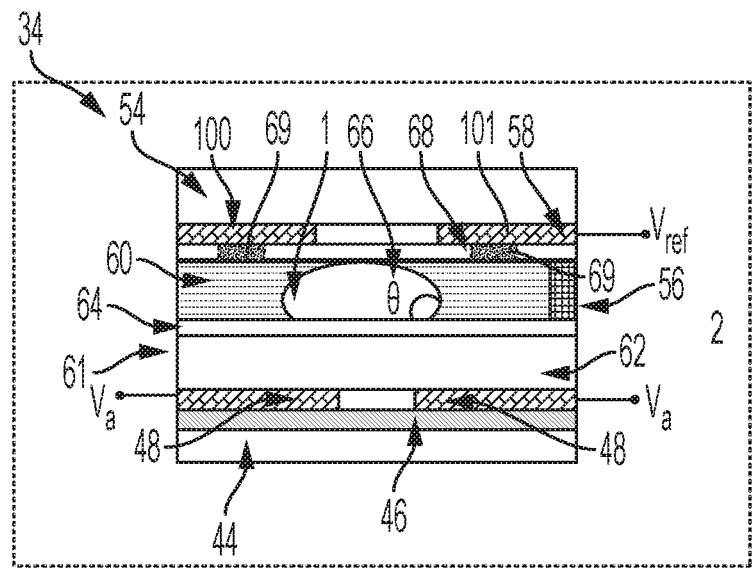
FIG. 3 is a cross-sectional side view of a portion of the AM-EWOD device.

FIGS. 2 and 3 illustrate the AM-EWOD device 34.

As seen in FIG. 2, the AM-EWOD device 34 has a first substrate 44 (which is the lowermost substrate in FIGS. 2 and 3) with thin film electronics 46 disposed upon the first substrate 44. An array 50 of actuation electrodes 48 are supported by the first substrate 46 on top of the thin film electronics 46. The thin film electronics 46 are arranged to drive the actuation electrodes 48.

The array 50 of actuation electrodes 48 may be an X by Y rectangular array, where X and Y are any integers. The actuation electrodes 48 may be formed, for example, from indium tin oxide (ITO) or another transparent metal oxide, or a metal, or any other electrically conductive material.

The AM-EWOD device 34 has a first substrate also includes a second substrate 54 (which is the uppermost substrate in FIGS. 2 and 3) separated by a spacer 56 from the first substrate 44. As described further below, droplets 1 are disposed between the first substrate 44 and a second substrate 54. A single droplet is shown in FIGS. 2 and 3 but in general multiple droplets 1 are present.

The layered structure of the AM-EWOD device 34 is best seen in FIG. 3 which illustrates a portion thereof including two actuation electrodes 48 supported by the first substrate 44. The actuation electrodes 48 may be formed from a patterned layer of conductive material.

An insulator layer 61 comprising a layer 62 of electrically insulating material coated by a hydrophobic material 64 is disposed on the first substrate 44, covering the actuation electrodes 48. The hydrophobic material 64 forms an outermost hydrophobic surface of the insulator layer 61.

The second substrate 54 faces the hydrophobic surface of the insulator layer 61. The second substrate 54 supports a layer 58 of conductive material that is deposited on the surface of the second substrate 54 facing the insulator layer 61. The layer 58 of conductive material is patterned to form more electrodes, as described in more detail.

The second substrate 54 is coated by a hydrophobic material 68 that covers the layer 58 of conductive material and forms a further hydrophobic surface facing the hydrophobic surface of the insulator layer 61.

The hydrophobic materials 64 and 68 may be formed by any suitable materials (which may be the same or different), for example a fluoropolymer.

The droplets 1 are received in the AM-EWOD device 34, disposed within a fluid medium 60. The droplets 1 and the fluid medium 60 are disposed on the hydrophobic surface of the insulator layer 61 and on the further hydrophobic surface of the hydrophobic material 68 that coats the second substrate 54. In this manner, the droplets 1 are sandwiched between the first and second substrates 44 and 54, which constrain the shape of the droplets 1. This improves the degree of control of the droplets 1 by the actuation signals applied to the actuation electrodes 48 in the manner described below.

The droplets 1 have a contact angle 66 with the hydrophobic surface of the insulator layer 61. The contact angle 66 is determined by the balancing of the surface tension components (1) from the hydrophobic surface to the liquid of the droplets 1 ($\Gamma_{SL}$) interface, (2) from the liquid of the droplets 1 to the surrounding fluid medium 60 ($\Gamma_{LG}$) interface, and (3) from the hydrophobic surface to the surrounding fluid medium 60 ($\Gamma_{SG}$) interface. Where no voltages are applied, the contact angle 66 satisfies Young's law, and is of size θ given by the equation $\cos\theta = ((\Gamma_{SG} - \Gamma_{SL})/\Gamma_{LG})$.

Accordingly, the actuation electrodes 48 are capable of electro-wetting the droplets 1 when actuation signals are applied to the actuation electrodes 48. The actuation signals create electrical forces that effectively control the hydrophobicity of the hydrophobic surface of the insulating layer 61, and thereby energise the droplet 1. In such an energised state, the droplets 1 will have a shape that is modified compared to when the droplets 1 are in a lower energy state, i.e. a state in which the actuation signals provide less or no energy to the droplets 1.

Such references to the shape being modified may refer to the shape in the plane of the AM-EWOD device 34, i.e. parallel to the hydrophobic surface of the insulator layer 61. Although energy supplied by the actuation signals will modify the three-dimensional shape of the droplets 1, the shape is most greatly affected in the plane of the AM-EWOD device 34, being the direction in which the actuation electrodes 48 are arrayed.

Similarly, references to the shape being modified compared to when in a lower energy state may refer to the shape of the contact line of the droplets 1. In this context, the term "contact line" has its normal meaning of the line along which the interface between the droplet 1 and the fluid medium 60 contacts the hydrophobic surface of the insulating layer 61 above the actuation electrodes 48.

By selective control of the pattern of actuation signals applied to the selected actuation electrodes 48, the droplets 1 may be manipulated and moved in the lateral plane between the first and second substrates 44 and 54. In general terms, such manipulation of droplets 1 in this manner may apply techniques known for EWOD devices.

The actuation signals may take any form suitable for electro-wetting the droplets 1. Typically, the actuation signals may be AC actuation signals, but in general they could also be DC voltage potentials with respect to a reference voltage. While applying the actuation signals, a reference signal is applied to a reference electrode 59 elsewhere in the AM-EWOD device, as described further below.

The reference signal may take any suitable form. In one example, the reference signal may be a fixed reference voltage. In another example where the actuation signals are AC actuation signals, the reference signal may be an AC reference signal which is in anti-phase with the AC actuation signals. In this example, the magnitude of the potential difference between the actuation electrodes 48 and the reference electrode 59 is increased, for example being doubled when the AC actuation signals and the AC reference signal are of equal magnitude, compared to a reference signal that is a fixed reference voltage.

Figures 4A, 4B:
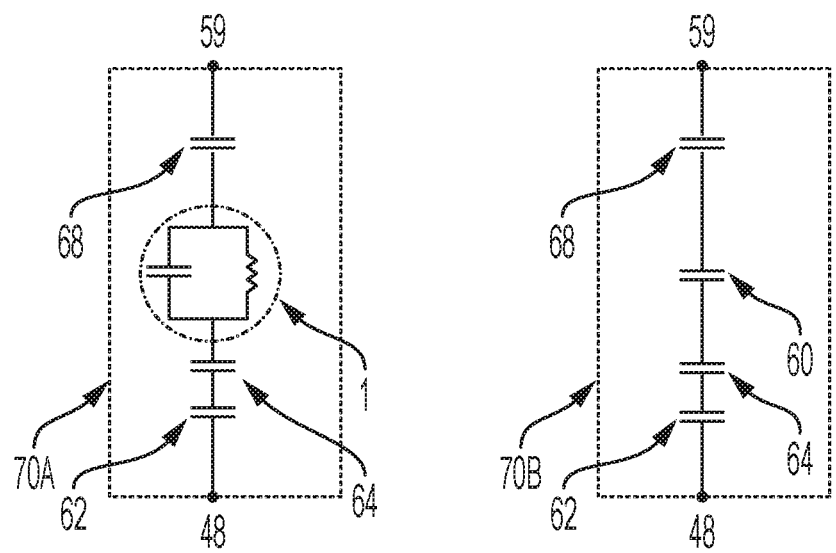
FIGS. 4A and 4B are diagrams of a circuit representation of the electrical load presented at the actuation electrode when a liquid droplet is present and not present, respectively.

FIG. 4A shows a simplified circuit representation of the electrical load 70A between the actuation electrode 48 and a reference electrode 59 in the case where a droplet 1 is present. The droplet 1 can usually be modelled as a resistor and capacitor in parallel. Typically, the resistance of the droplet 1 will be relatively low (e.g. if the droplet contains ions) and the capacitance of the droplet will be relatively high (e.g. because the relative permittivity of polar liquids is relatively high, e.g. ~80 if the droplet 1 is aqueous). In many situations the droplet resistance is relatively small, such that at the frequencies of interest for electro-wetting, the droplet 1 may function effectively as an electrical short circuit. The hydrophobic materials 64 and 68 have electrical characteristics that may be modelled as capacitors, and the insulating material of the layer 62 may also be modelled as a capacitor. The overall impedance between the actuation electrode 48 and the reference electrode 59 may be approximated by a capacitor whose value is typically dominated by the contribution of the insulating material of the layer 62 and hydrophobic materials 64 and 68 contributions, and which for typical layer thicknesses and materials may be on the order of a pico-Farad in value.

FIG. 4B shows a circuit representation of the electrical load 70B between the actuation electrode 48 and the reference electrode 59 in the case where no droplet 1 is present. In this case the droplet components are replaced by a capacitor representing the capacitance of the non-polar fluid 60 which occupies the space between the top and first substrates. In this case the overall impedance between the actuation electrode 48 and the reference electrode 59 may be approximated by a capacitor whose value is dominated by the capacitance of the non-polar fluid and which is typically small, of the order of femto-Farads.

For the purposes of driving and sensing the actuation electrodes 48, the electrical loads 70A and 70B overall function in effect as a capacitor, whose value depends on whether a droplet 1 is present or not at a given actuation electrode 48. In the case where a droplet is present, the capacitance is relatively high (typically of order pico-Farads), whereas if there is no droplet 1 present the capacitance is low (typically of order femto-Farads). If a droplet partially covers a given electrode 48 then the capacitance may approximately represent the extent of coverage of the actuation electrode 48 by the droplet 1.

Figure 5:
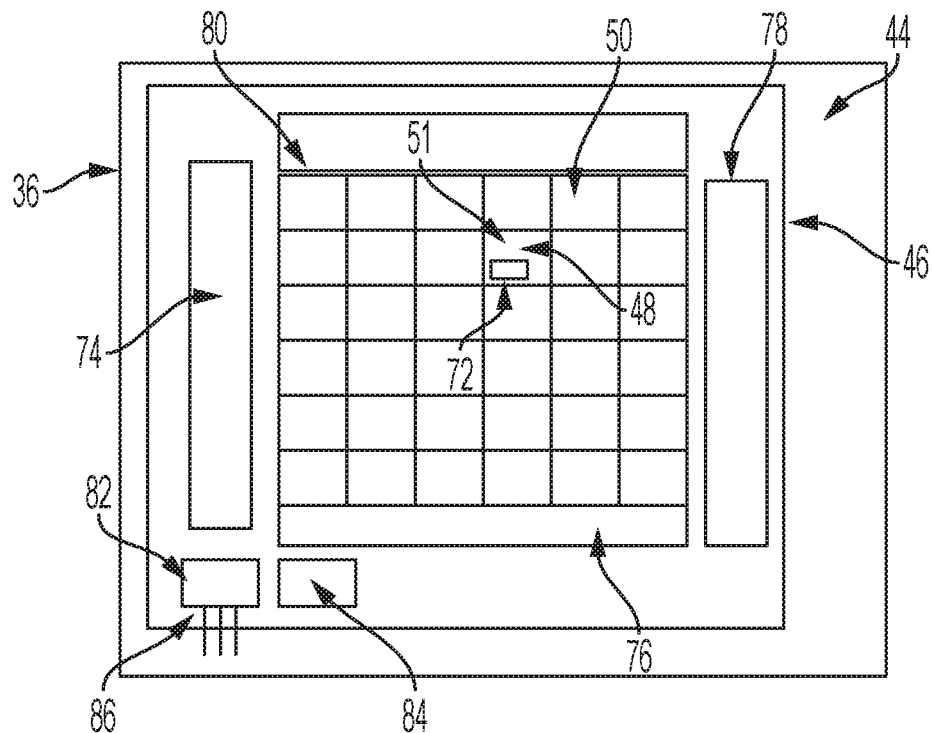
FIG. 5 is a plan view of thin film electronics in the AM-EWOD device.

FIG. 5 illustrates the arrangement of the thin film electronics 46 in the AM-EWOD device 34. The thin film electronics 46 is located on the first substrate 44 and comprises an active matrix arrangement of array elements 51 each comprising an array element circuit 72 for controlling the electrode potential of a corresponding actuation electrode 48. Integrated row driver 74 and column driver 76 circuits are also implemented in thin film electronics 46 to supply control signals to the array element circuit 72. In this manner, the array element circuit 72 may perform a function of selectively, under the control of the control system 37, actuating the actuation electrode 48 to applying an actuation signal to the actuation electrode 48. Thus, the control system 37 controls the actuation signals applied to the actuation electrodes 48, such as required voltage and timing signals to perform droplet manipulation operations.

Figure 6:
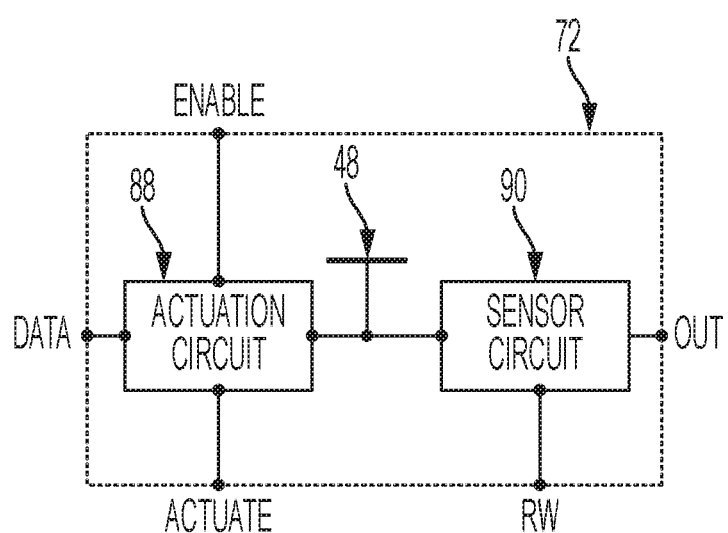
FIG. 6 is a diagram of an array element circuit of the AM-EWOD device.

FIG. 6 illustrates the arrangement of the array element circuit 72 present in each array element 51. The array element circuit 72 contains an actuation circuit 88, having inputs ENABLE, DATA and ACTUATE, and an output which is connected to an actuation electrode 48.

A serial interface 82 may also be provided to process a serial input data stream and facilitate the programming of the required voltages to the actuation electrodes 48 in the array 50. A voltage supply interface 84 provides the corresponding supply voltages, second substrate drive voltages, and other requisite voltage inputs. A number of connecting wires 86 between the first substrate 44 and external control electronics, power supplies and any other components can be made relatively few, even for large array sizes. Optionally, the serial data input may be partially parallelized. For example, if two data input lines are used the first may supply data for columns 1 to X/2, and the second for columns (1+X/2) to M with minor modifications to the column driver circuits 76. In this way the rate at which data can be programmed to the array elements 51 is increased, which is a standard technique used in Liquid Crystal Display driving circuitry.

Droplet Interface Sensing

Figure 7:
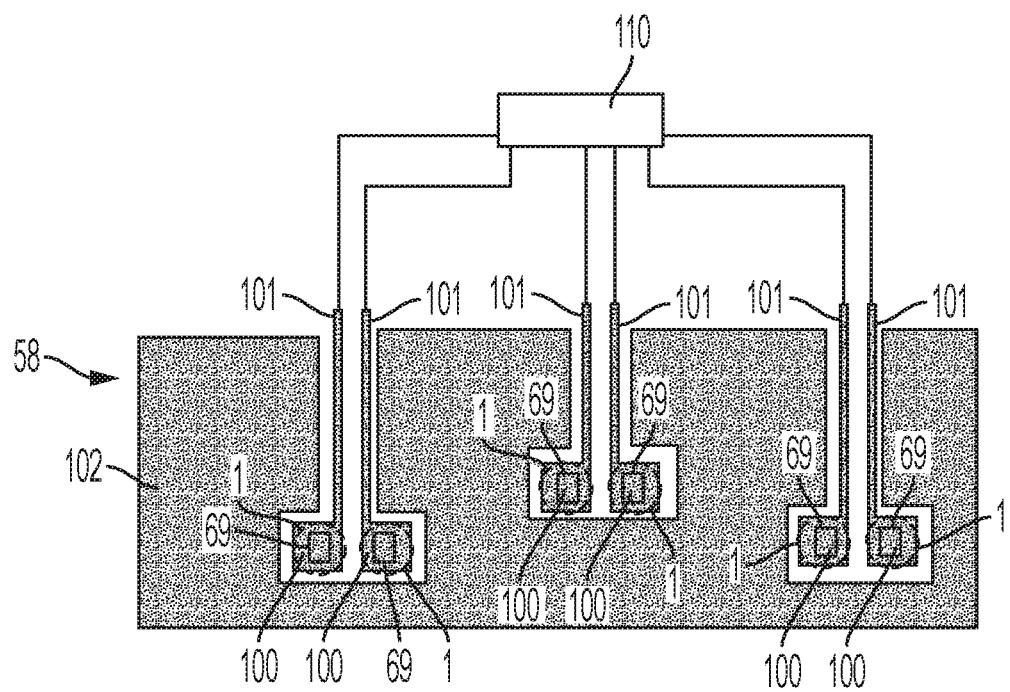
FIG. 7 is a plan view of a layer of conductive material formed on a second substrate of the AM-EWOD device.

FIG. 7 shows how the layer 58 of conductive material is patterned to form sensor electrodes 100, conductive tracks 101, and further electrodes 102 which are therefore deposited on the second substrate 54 and supported thereby.

The sensor electrodes 100 are arranged to make an electrical connection with respective droplets 1. The provision of the sensor electrodes 100 is a convenient and reliable way to make electrical connections to the droplets 1, for example to take electrical measurements between the droplets 1 across a droplet interface formed therebetween. In contrast, such a type of electrical connection is not possible from the actuation electrodes 58 due to the presence of the insulating layer 61 including layer 62 of electrically insulating material between the actuation electrodes 48 and the droplets 1.

The hydrophobic material 68 that covers the layer 58 of conductive material coating the second substrate 54 is provided with apertures 69 that expose part of the sensor electrodes 100, although more generally the apertures may be larger and expose the entirety of the sensor electrodes 100. The apertures 69 in the hydrophobic material 68 assist in making an electrical contact between the sensor electrodes 100 and the droplets 1. The fluid medium 60 and/or the liquid of the droplets 1 can flow into apertures 69, and have a lower electrical impedance than the hydrophobic material 68, thereby providing a conductive path.

Such apertures 69 may have the additional advantage of acting as a hydrophilic patch which helps to pin droplets 1 in position if the electrodes are de-actuated or the device is de-powered.

Such apertures 69 may be created by selective removal of the hydrophobic material 68, for example by means of a dry etch process or lift off process.

However, the apertures 69 are not essential and instead an electrical connection between the sensor electrodes 100 and the droplets 1 can be made through the hydrophobic material 68, which may be of sufficiently low impedance (either real or imaginary parts) that an electrical measurement can still be taken through it. In that case, the thickness and material properties of the hydrophobic material 68 are chosen accordingly.

The sensor electrodes 100 are arranged in sets and the sensor electrodes 100 of each set are sized and shaped to make an electrical connection with droplets 1 between which a droplet interface is formed in a respective system of droplets 1. This may be achieved by the area of the sensor electrodes 100 being similar to the area enclosed by the contact line of the droplets 1 with the sensor electrodes 100, and distance between the centre of the sensor electrodes 100 within each set and being similar to the distance between the centre of the droplets 1 in the formed system. Each set of sensor electrodes 100 may be aligned with a respective system of droplets 1 for making electrical connections to respective droplets 1 in that system of droplets 1. Thus, the control system 37 may be configured to form plural systems of two or more droplets 1, where each system of droplets 1 is aligned with a respective set of sensor electrodes 100.

By way of illustration, FIG. 7 shows three sets of two sensor electrodes 100 and three systems of two droplets 1 formed in alignment with the sensor electrodes 100 of the respective sets. However, in general, there could be any number of sets of sensor electrodes 100, and the sets could contain any number of sensor electrodes 100 in dependence in the number of droplets 100 to be included in each system.

As a result of this configuration, systems of droplets 1 may be formed in parallel and experiments may be performed thereon in parallel using the respective sets of sensor electrodes 100. In general any number of systems of droplets 2 may be formed, for example two or more, up to large numbers of order tens of thousands.

The conductive tracks 101 are connected to the sensor electrodes 100 and extend to the edge of the layer 58 of conductive material where an electrical connection is made to a droplet interface sensor system 110 described further below. Thus, the conductive tracks 101 provide an electrical connection from the sensor electrodes 100 to the droplet interface sensor system 110.

The further electrode 102 extends around the sensor electrodes 100 and the conductive tracks 101.

The further electrode 102 may function as the reference electrode 59 in the circuit representations shown in FIGS. 4A and 4B. In that case, the control system 37 is connected to the further electrode 102 and is arranged to apply a reference signal to the further electrode 102, while applying actuation signals to the actuation electrodes 48.

However, the further electrode 102 is not essential. When the further electrode 102 is absent, or even when the further electrode 102 is present, a different electrode(s) may function as the reference electrode 59. In one example, the sensor electrodes 100 may function as the reference electrode 59.

In another example, a reference electrode 59 may be provided elsewhere between the first and second substrates 44 and 54, for example as a separate element such as an in-plane reference electrode. In any such example, the control system 37 is connected to the reference electrode 59, e.g. the sensor electrodes 100, and is arranged to apply a reference signal to the reference electrode 59, while applying actuation signals to the actuation electrodes 48. In such an arrangement, unactuated actuation electrodes 48 on the first substrate 44 may operate as a reference and droplets 1 can be moved without needing a reference electrode on the second substrate 54.

The reader 32 further comprises the droplet interface sensor system 110 including a measurement unit 111 which is connected to the sensor electrodes 110 and takes electrical measurements between sensor electrodes 110 that are electrically connected to respective droplets 1, across droplet interfaces formed therebetween. The measurement unit 111 is typically controlled to take electrical measurements out while actuation signals are not applied to the actuation electrodes 48. This has the advantage of reducing the risk of the actuation signals affecting the electrical measurements, for example by physically affecting or damaging the system of droplets being measured or by causing electrical interference with the measurement unit 111.

The elements of the thin film electronics 46 are electrically isolated from the sensor electrodes 100 and the measurement unit 111, so do not participate in taking of the electrical measurements.

Any suitable electrical measurements may be taken, for example impedance, current or capacitance measurements. In a possible configuration, the electrical measurements may be taken by applying a voltage and measuring the current sourced through one of the sensor electrodes 100, whilst the other sensor electrode 100 is grounded. The real and imaginary parts of the electrical impedance of the droplet interface 2 may thus be determined.

The measurement unit 111 may be formed by suitable electronic components suitable for droplet interface experiments, for example including detection channels including amplifier arrangements. In one example, the measurement unit 111 may comprise a patch clamp arrangement. In another example, the measurement unit 111 may have the same construction as the signal processing function described in WO-2011/067559.

The electrical measurements may be taken in a frequency range from a lower limit to an upper limit, wherein the lower limit is 1 Hz, 10 Hz or 100 Hz and the upper limit is 10 MHz, 100 KHz or 10 KHz, in any combination.

The measurement unit 111 may be arranged to apply a potential difference between a respective pair of sensor electrodes 100 across which measurements are taken, while taking those measurements.

The measurement unit 111 is controlled by the control system 37 to take electrical measurements from any of the systems of droplets 1 after they have been formed in the AM-EWOD device 34 under the control of the control system 37.

The electrical measurements may be of any suitable type, for example being impedance measurements and/or measurements of ion current flow across the droplet interface. Where the measurements are taken across droplet interface comprising a membrane of amphipathic molecules having a transmembrane pore inserted therein, the electrical measurements may be, for example, measurements of ion current flow between the droplets through the transmembrane pore and/or electrical measurements that are dependent on an analyte that interacts with the transmembrane pore.

The measurements may be optical or a combination of optical and electrical, such as disclosed by Soni G V et al., Rev Sci Instrum. 2010 January; 81(1):014301 and T Gilboa and A Meller, Analyst, 2015, 140, 4733-4747.

The droplet interface sensor system 110 may further comprise an analysis system 112 configured to process the electrical measurements that are dependent on an analyte that interacts with a transmembrane pore, in order to analyse the analyte. For example, where the analyte is a polymer comprising polymer units, the analysis system may be configured to process the electrical measurements to derive estimated identities of the polymer units of the polymer. The analysis system 112 may process the electrical measurements using any suitable known technique, some examples of which are described further below.

The analysis system 112 may be formed by an appropriate combination of (1) a hardware stage, for example a field programmable gate array (FPGA), to pre-process the electrical measurements supplied as a signal from the measurement unit 111, and (2) a processor for processing the signals supplied from the hardware stage. The processor may be any suitable form of processing device. The processor may be implemented within the reader 32 as shown in FIG. 1, and may execute software which may be stored in the storage device 40. As an alternative, the processor could be implemented by a processing device, for example a conventional computer apparatus, external to the reader 32.

By way of example, the measurement unit 111 and the analysis system 112 may have the same construction as the signal processing function described in WO-2011/067559.

The droplet interface sensor system 110 may be combined with other types of measurement system to take measurements, for example capacitance measurements from the actuation electrodes, measurements from additional electrodes (not shown) and/or measurements using electromagnetic radiation, including but not limited to absorbance or emission infra red, ultraviolet, which techniques may employ labelled dyes or antibodies, and/or fluorescence resonance energy transfer (FRET).

Droplet Sensing

The array element circuit 72 also may contain a droplet sensor circuit 90, which is in electrical communication with the actuation electrode 48. The droplet sensor circuit 90 provides a sensing capability for detecting the presence or absence of a droplet 1 in the location of each actuation electrode 48. In this manner, the array element circuit 72 may also perform a function of sensing the presence or absence of a droplet 1 at the location of the array element 51 during manipulation of the droplets 1. However, due to the presence of the insulating layer 61 including layer 62 of electrically insulating material between the actuation electrodes 48 and the droplets 1, it may be difficult or inconvenient to take electrical measurements suitable for studying a droplet interface or processes occurring at a droplet interface.

The droplet sensor circuit 90 may conveniently employ capacitive sensing using an impedance sensor circuit. The droplet sensor circuit 90 may include impedance sensor circuitry of the type known in the art, as described for example in U.S. Pat. No. 8,653,832 and GB-2,533,952. As described therein, droplets 1 may be actuated by means of electro-wetting and may be sensed by capacitive or impedance sensing means. Typically, capacitive and impedance sensing may be analogue and may be performed simultaneously, or near simultaneously, at every array element 51. By processing the returned information from such a sensor (for example in the application software in the storage device 40 of the reader 32), the control system 37 can determine in real-time, or almost real-time the position, size, centroid and perimeter of each droplet 1 present in the AM-EWOD device.

Alternatively, such sensing may be performed by some other means, for example optical or thermal means. An alternative to the droplet sensor circuit 90 is to provide an external sensor such as an optical sensor that can be used to sense droplet properties, as is known in the field of electro-wetting devices.

The control system 37 generates and outputs control signals for the droplet sensor circuit 90 to perform sensing operations during manipulation of the droplets 1. Integrated sensor row addressing 78 and column detection circuits 80 are implemented in the thin film electronics 46 for the addressing and readout of the droplet sensor circuit 90 in each array element circuit 72. Typically, the read-out of the droplet sensor circuit 90 may be controlled by one or more addressing lines (e.g. RW) that may be common to array elements 51 in the same row of the array 50, and may also have one or more outputs, e.g. OUT, which may be common to all array elements 50 in the same column of the array 50.

The control system 37 may use the output of the of the droplet sensor circuit 90 to control the timing of the application of actuation signals to the actuation electrodes 48 when manipulating droplets 1.

Formation of Droplet Interfaces

The control system 37 is configured to control the AM-EWOD device 34 to form systems of droplets 1 having one or more droplet interfaces 2 between pairs of droplets 1 as follows.

Firstly, the control system 37 controls the droplet preparation system 35 to form the droplets 1 in the AM-EWOD device 34, as needed for respective systems of droplets 1. The droplets 1 may be prepared from any appropriate reagents, as required for the experiments being performed. Suitable reagents are described below.

Next, the control system 37 controls the application of actuation signals to the actuation electrodes 48 to form the systems of droplets 1.

It has been considered to simply apply actuation signals to manipulate the droplets 1 by simply moving the droplets across the array 50 of actuation electrodes 48 from where they are formed towards each other and into contact. However, in that case, the droplets 1 have a tendency to fuse and it is difficult to maintain the droplet interface between the droplets 1. Optimising of conditions to promote formation of a droplet interface 2 is difficult as electro-wetting is dependent on several factors which are likely to change between samples, such as salt concentration, droplet reagents (especially membrane components) and droplet size.

Accordingly, a different method is implemented employing two stages, as will now be described.

An example of the method is shown in FIGS. 8 to 12 which shows a plan view of a pair of droplets 1 on an array 50 of actuation electrodes 48 successively as the droplets are manipulated during the method. In particular, FIGS. 8 to 12 show the contact lines of the droplets on the array 50 of actuation electrodes 48. FIGS. 8 to 12 also show the pattern 53 of actuation signals applied, by hashing of the selected actuation electrodes 48 to which actuation signals are applied 53. This example is merely for illustration and is not limitative. Various changes may be made, for example to the size of the droplets 1 and the pattern of actuation signals may be made. It is also noted that FIGS. 8 to 12 relate to an example in which the liquid of the droplets 1 is polar and the fluid medium 50 is apolar, with the result that the actuation electrodes 48 to which actuation signals are applied are electro-wet. In a notional alternative in which the liquid of the droplets 1 is apolar and the fluid medium 50 is polar, then the pattern of actuation signals would be inverted with the result that the actuation electrodes 48 to which actuation signals are not applied attract the apolar droplets.

By way of background, it is noted that, in a relaxed state of the droplets 1 where they are not electro-wet by the application of actuation signals to the actuation electrodes 48, the droplets 1 would take the shape of lowest surface energy, which would generally be a circular shape where the hydrophobic surface of the insulator layer 61 has uniform properties.

In a first stage of the method, actuation signals are applied to the selected actuation electrodes 48 to energise the one, or preferably both, of two droplets 1 between which a droplet interface is to be formed. For clarity of description, the case of energising both of the two droplets 1 will now be described.

In the energised state, the shape of the droplets 1 is modified compared to a shape of the droplets 1 in the lower energy state of the droplets 1. In such an energised state, the two droplets 1 are moved into proximity with a gap 3 therebetween. Due to the gap 3, the droplets 1 do not contact each other at this time.

The first stage of the method may be performed under feedback control from the droplet sensor circuit 90.

Figures 8, 9:
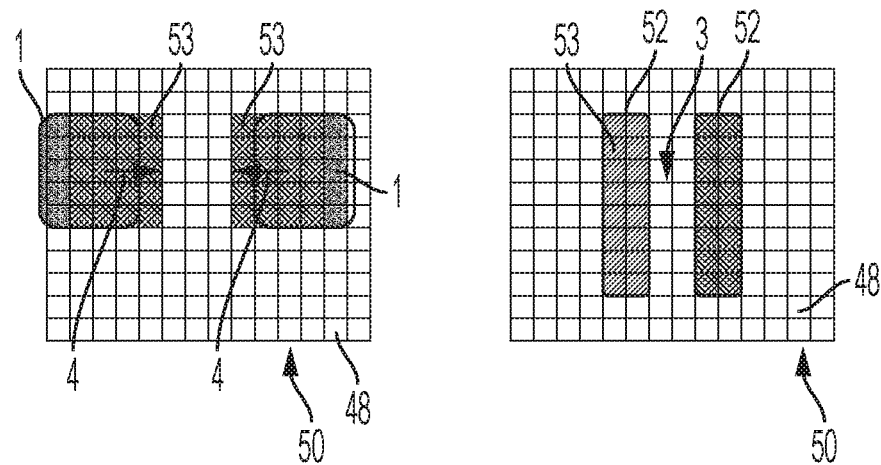

Examples of the processes applied in the first stage are shown in FIGS. 8 to 10, as follows.

FIG. 8 shows a step where a pattern 53 of actuation signals is applied to a square 4-by-4 group of actuation electrodes 48. This energises the two droplets 1 to form a corresponding shape that is generally also square but with some rounding of the corners that minimises the surface energy of droplets 1. FIG. 8 also shows how the droplets 1 may be moved together. In particular, FIG. 8 shows the case that the pattern 53 of actuation signals is applied to a group of actuation electrodes 48 that is shifted relative to the previous step. This has the result of moving the droplets 1 towards the group of actuation electrodes 48, in the direction of the arrows 4. In this manner, the droplets 1 may be shaped and may be moved.

FIG. 9 shows a step where a pattern 53 of actuation signals is applied to a rectangular 2-by-8 group of actuation electrodes 48. This energises the two droplets 1 to form a corresponding shape that is generally also rectangular but with some rounding of the corners that minimises the surface energy of the droplets 1. In this step, the rectangular 2-by-8 groups of actuation electrodes 48, and hence the droplets 1, are in proximity with a gap 3 of two columns of actuation electrodes 48.

FIG. 10 shows a step subsequent to that shown in FIG. 9 where the actuation signals have the same pattern 53 except that one of the 2-by-8 groups of actuation electrodes 48 is shifted by one column of actuation electrodes 48, so that the rectangular 2-by-8 groups of actuation electrodes 48, and hence the droplets 1, are in proximity with a gap 3 of a single column of actuation electrodes 48. In this example, this is the final step of the first stage of the method.

In a second stage of the method, the applied actuation signals are changed such that the energy of the droplets 1 is lowered into a lower energy state.

In this stage, the change is preferably to apply no actuation signals to actuation electrodes 48 that affect the droplets 1. In that case, no energy is supplied to the droplets 1 from the actuation electrodes 48, so the lower energy state is a state of minimum energy of the droplets 1 where their shape after relaxation is affected solely by the material properties. Alternatively, in the change may in principle be to apply actuation signals that energise the droplets 1 but to a lesser degree, so that the droplets 1 relax and their shape changes but to a lesser degree than when no actuation signals are applied to actuation electrodes 48 that affect the droplets 1.

As a result of being placed in a lower energy state, the surfaces of the droplets 1 that face one another across the gap 3 relax into the gap 3 and contact each other, thereby forming a droplet interface 2 between the two droplets 1. Thus, the movement of the surface of the droplets 2 is caused by relaxation from the energised state of the droplets 1 generated in the first stage. This is a passive process that provides reliable formation of the droplet interface 2. The rate to which a droplet 1 relaxes may be dependent upon one or more factors, such as relative viscosity of the liquid of the droplet 1 to that of the fluid medium 50, the size of the droplet 1 and/or the size of the gap 3.

The device geometry (size of droplets 1, height of gap between the hydrophobic surfaces, etc.) and surface tensions at the droplet interfaces 2, which are themselves dependent on choice of materials and material properties, are arranged such that when the surfaces of the droplets 1 touch, the droplets 1 do not fuse or coalesce, but rather a droplet interface 2 is formed. The geometry of the patterns of actuation signals and spatial dimensions of the droplets 1 will typically be arranged such that the droplet interface 2 is formed with a minimal surface area.

The applied actuation signals may be changed in any manner to de-energise the droplets 1. Where the actuation signals that are applied to electro-wet the actuation electrodes are AC actuation signals, then the change is desirably to replace the AC actuation signals which energised the droplets 1 by DC potentials, for example a ground potential, or by floating potentials. This has the benefit that AC signals are no longer applied to the actuation signals, which assists in forming of the droplet interface 2 because the presence of AC electric fields resulting from AC signals increases the risk of the droplet interface 2 rupturing and causing the droplets 2 to fuse when the surfaces of the droplets 2 come into contact.

Other changes which de-energise the droplets 1 may alternatively be made. An alternative is to remove all power from the array 50 of actuation electrodes 48. However, it may be preferable to apply a DC potential to assist in shielding the droplet interface 2 from unwanted environmental electro-magnetic interference.

The present inventors have appreciated that it is preferable not to de-actuate the droplets in the conventional way by applying AC voltage waveforms, since resultant perturbations may damage a droplet interface 2 or may interfere with electrical measurements through the droplet interface 2.

Examples of the processes applied in the second stage are shown in FIGS. 11 and 12, as follows.

FIG. 11 shows a step where the pattern of actuation signals is changed compared to that shown in FIG. 10 by ceasing the application of actuation signals to the two 2-by-8 groups of actuation electrodes 48 and instead applying a DC potential or floating potential. FIG. 11, shows the droplets 1 at the moment where the change is made, when the droplets instantaneously have the same generally rectangular shape as before. However, the droplets then relax into the lower energy state shown in FIG. 12. In the absence of the other droplet 1, each droplet 1 would take its own lower energy state which is generally circular, but the centre of mass of the droplets 1 remains in generally the same location. Thus, in relaxing towards those lower energy states, the surfaces of the droplets 1 that face one another across the gap 3 relax into the gap 3 and contact each other, thereby forming a droplet interface 2.

The particular shapes of the droplets 2 in the energised state shown in FIGS. 8 to 10 are not limitative, and in general any shape could be used that allows relaxation of the droplets 1 into contact to form a droplet interface. Typically, the shape of the energised contact line of the droplets 2 may be elongate, with the gap 3 extending along a length of the elongate shape. Any elongate shape may be chosen, for example a rectangular shape as shown in FIG. 9, an ellipsoidal shape, or a more complex shape. Shapes which are not elongate may also be used, for example a square shape as shown in FIG. 8.

The exact shape of the droplets 1 is selected by control of the pattern of the actuation signals, but may vary from that due to the surface tension between the droplets 1 and the fluid medium 50, which will depend on the material properties.

Where the shape of the energised contact line of the droplets 2 is elongate, the shape of the energised droplets 1 may have an aspect ratio of at least 2:1, preferably at least 4:1 or at least 8:1. In general, increasing the aspect ratio increases the degree of movement of the surface of the droplets 1 when they are de-energised, thereby assisting in bringing the droplets 1 into contact.

The gap 3 between the droplets 1 in the first stage is chosen such that the two droplets 1 are sufficiently close, although not contacting, that they form a droplet interface 2 when placed in the lower energy state. The width of the gap 3 when the droplets 1 are brought into proximity is chosen to allow the droplets 1 to come into contact when the pattern of actuation signals is changed. This may depend on the same of the droplets 1 in the energised state. Typically, the width of the gap 3 when two droplets 1 are brought into proximity may be chosen so that the centroids of the two droplets 1 are separated by a distance less than the combined radii of the droplets 1 along a line between the two centroids in the lower energy state of the droplets 1.

The gap 3 may have a width of a single row or column of actuation electrodes 38 in the array 50, or two or more rows or columns of actuation electrodes 38 in the array 50.

To assist these processes, the area enclosed by the contact line of the droplets 1 is desirably large compared to the area of the actuation electrodes 38. This increases the resolution of the control of the shape in the energised state of the droplets 1, assisting in allowing movement of the droplets 1 across the array and movement of the surfaces of the droplets 1 into contact on relaxation. The AM-EWOD device 1 is therefore designed with actuation electrodes 48 that are sized having regard to typical sizes of droplets 1 desired to be used experimentally. A particular advantage of the active matrix arrangement is that it allows application of actuation patters of actuation signals at a resolution that is high compared to the size of the droplets 1.

Typically, the area enclosed by the contact line of the droplets 1 in the lower energy state is at least two times the area of an actuation electrode 48, preferably at least 5 times, at least 10 times or at least 20 times. Thus, the area enclosed by the contact line of the droplets 1 in the lower energy state may cover at least two actuation electrodes 48, preferably at least 5 actuation electrodes 48, at least 10 actuation electrodes 48 or at least 20 actuation electrodes 48.

The above description refers to energising both droplets 1 for ease of description, but alternatively a droplet interface 2 may be formed by only energising one of the two droplets 1 in the first phase. In that case, on changing the actuation signals in the second phase, a surface of that one droplet 1 relaxes into contact with a stationary surface of the other droplet 1.

Systems of Droplets

Above, there is described formation of a single droplet interface 2 between a system of two droplets 1. Using similar methods, plural droplet interfaces 2 may be formed between respective pairs of droplets in a system of three or more droplets 1. Droplet interfaces 2 may be formed sequentially by bringing droplets 1 into contact successively or simultaneously. By way of example, FIG. 13 illustrates an example of forming a system of three droplets 1 having two droplet interfaces 2 that are formed sequentially, and FIG. 14 illustrates an example of forming a system of three droplets 1 having two droplet interfaces 2 that are formed simultaneously. In each of these examples, the droplet interfaces 2 are formed using the method described above.

In general, the configuration of the formed system of droplets 1 is chosen in a manner to perform a desired experiment. In such formed systems, the droplets 1 may be arranged in series with droplet interfaces 2 similarly in a series, as shown for example in the systems of three droplets 1 shown in FIGS. 13 and 14. Alternatively, in the formed systems, the droplets 1 may have more complex arrangements or clusters, two non-limitative examples of which are shown in FIGS. 15 and 16.

In such systems of droplets 1, the droplets 1 may be or of equal or unequal volume and the droplets 1 may have the same or different constituents.

One or more droplets in a system may comprise transmembrane pore capable of insertion into a droplet interface 2. Typically, after formation of a droplet interface 2, the transmembrane pore inserts spontaneously into the droplet interface 2, after which electrical measurements may be taken. One or more droplets 1 in a system may comprise an analyte that interacts with the transmembrane pore.

There are a number of advantages in use of the apparatus 1 to form a droplet interface 2 and subsequently take electrical measurements on the droplet interface 2 thus formed, in particular when making a system of three or more droplets 1 having plural droplet interfaces 2. For example relatively small sample volumes may be used as compared to some other techniques that involve formation of an array of planar membranes. It allows the possibility of using long lengths of polynucleotide as there is a reduced chance of shearing as library preparation may occur on the same device as measurement. Given that a sample does not need to be transferred, the contamination risks are lower. Because all of the sample is contained in either one or both of the droplets 1, there is small sample loss, which can be recovered. As electro-wetting is used for all liquid manipulation, the need for pumps or other moving parts is eliminated. Since droplet positioning is controlled through programmed scripts, sample preparation can be automated. Droplets of DNA sample can then be supplemented with desired components including polymer vesicles, reagents, pores and analytes.

In one type of experiment, droplets 1 may be periodically split off from a volume of sample, for example to monitor an ongoing reaction occurring in the sample. This provides for analysis with time, titration of reactant, change in conditions, etc.

Other advantages include:
- the ability to perform coupled library preparation/PCR with sensing/sequencing; ease of use library to sequence (automated, walk away)
- low contamination risks
- use of compartmentalised samples for library or sequencing
- permitting sampling different positions of sample/reaction, for example the length through a gel/mesh/diffusion barrier, positions on a cell sample and/or a concentration/thermal/density gradient.

Feedback and Modification

As described above, the apparatus 1 is suitable for forming droplet interfaces 2 in systems of droplets 1 and performing experiments on those droplet interfaces 2. Particular advantage is obtained by the control system 37 modifying a formed system of droplets 1 in response to outputs of the droplet interface sensor system 110. Thus, the system of droplets 1 may be modified to modify ongoing performance of the experiments using feedback from the experiment previously performed. This provides a powerful experimental tool, because the experiments may be adaptively performed.

Various outputs of the droplet interface sensor system 110 may be used to provide feedback, for example as follows.

The outputs of the droplet interface sensor system 110 that may be used include electrical measurements taken by the measurement unit 111. This provides a first type of control.

As the electrical properties are fundamental to the relevant processes such as formation of droplet interfaces and reactions occurring there, this first type of control allows those processes to be considered and adaptively modified. For example, electrical measurements taken by the sensor system may be used to determine whether a droplet interface 2 has been formed successfully.

The outputs of the droplet interface sensor system 110 that may be used include outputs of the analysis system 112. This provides a second type of control. As such analysis allows higher level information to be obtained, for example concerning an analyte being analysed, this second type of control provides powerful experimental adaption based on the results of the analysis.

The control system 37 may modify a formed system of droplets 1 in various ways, for example as follows.

The control system 37 may modify a formed system of droplets 1 by separating a droplet interface 2 between in the system. To do this, the control system 37 applies a pattern of actuation signals to the actuation electrodes 48 that moves apart one or both droplets between which the droplet interface 2 is formed. The separation of the droplets 1 separates the droplet interface 2.

Such separation may be used, for example, to stop an interaction occurring at the droplet interface 2. This may be done, for example, when the electrical measurements taken by the measurement unit 111 indicate that a droplet interface 2 has not been formed successfully or the outputs of the analysis system 112 indicate that an analysis has been completed, for example because an analyte has become depleted, or sufficient electrical measurements about a particular analyte have been taken.

The control system 37 may modify a formed system of droplets 1 by moving a new droplet 1 into contact with a current droplet 1 in the system of droplets 1 and forming a droplet interface 2 between the new droplet 1 and the current droplet 1. To do this, the control system 37 applies actuation signals to the actuation electrodes 48 using the same method as described above.

Such formation of a new droplet interface 2 may be used, for example, when the electrical measurements taken by the measurement unit 111 indicate that a droplet interface 2 has not been formed successfully so it desired to form a new droplet interface, or the outputs of the analysis system 112 indicate that an analysis at a droplet interface 2 has been completed and it is desired to obtain further measurements.

The control system 37 may modify a formed system of droplets 1 by moving a new droplet 1 into contact with a current droplet 1 in the system of droplets 1 and fusing the new droplet 1 and the current droplet 1. To do this, the control system 37 applies actuation signals to the actuation electrodes 48 that moves the new droplet 1 into contact with a current droplet 1 and causes them to fuse. The fusing of the droplets 1 may be achieved simply by the movement of the new droplet 1 into contact with a current droplet 1 without using the method described above to form a droplet interface. Alternatively, or additionally, the fusing of the droplets 1 may be achieved by applying an AC actuation signal that ruptures the droplet interface that would otherwise be formed between the new droplet 1 and the current droplet.

Such fusing of a new droplet 1 into a current droplet 1 of the system may be used, for example, to introduce new reagents into the current droplet 1, for example when one member of a redox couple in the one of the pairs of droplets 1 has become depleted.

When fusing a new droplet 1 in this manner, it may be that the new droplet 1 does not comprise amphipathic molecules at the interface between the liquid of the droplet 1 and the fluid medium 50.

These and other ways of modifying the formed system of droplets 1 may be used together in any combination, for example to perform a multi-stage experiment.

Although some specific applications are described above, these are not limitative and indeed one of the benefits of the feedback is that versatility. Some further non-limitative examples of applications are as follows:

Automated insertion of transmembrane pores
Adaption of a system of droplets 1 to unwanted insertion of pores or secondary pores
Control based on reaction/sample conditions
Promotion of droplet interface separation
Delivery of more sample or reagent
Delivery of a different sample
Delivery of more mediator to a droplet
Separation of a droplet 1 to take a sample elsewhere and/or to recover it and/or to return it to an original volume of sample
Change of reaction conditions (e.g. temperature, additive, quench/activate)
Taking of an alternative measurement (e.g. absorbance)
Return of sample to original volume
Performance of a new reaction on an analysed sample (or part thereof)
Control of multiple pore types and balancing of each for multiple membranes
Formation of membrane arrangements with multiple membranes and pores that interfaces with the same sample
Performance of an experiment only until sufficient information has been obtained, thereby increasing overall experimental throughput.
Queuing/pooling of samples, e.g. allowing delivery of library samples from a queue of samples on demand, and/or changing the queue order
Pooling of samples as a result of sequencing/sensing
Determination of which of plural samples to analyse
Determination of duration of run/success criteria
Determination of conditions for sample modification prior to membrane/pore analysis (e.g. type/concentration of library prep)
When droplets 1 are periodically split off from a volume of sample, use of the result of previous experiments as feedback to adapt reaction/sample conditions
Performance of directed evolution using membrane/pore as sensor Droplets in Fluid Medium Where reference is herein to droplets comprising liquid in a fluid medium, the liquid and the fluid medium may be chosen as follows. In general, any liquid that forms a droplet in a fluid medium may be used, but some possible materials are as follows.

The fluid medium may in principle be a gaseous medium, but is preferably a liquid medium.

In some cases, and often when the fluid medium is a liquid medium, one of the liquid and the fluid medium is polar, and the other of the liquid and the fluid medium is apolar. Preferably, the liquid of the droplets is polar, and the fluid medium is apolar.

When one of the liquid and the fluid medium is polar, the polar medium is typically an aqueous liquid that comprises water. The aqueous liquid may further comprise one or more solutes. The aqueous liquid may for instance comprise a buffer in order to regulate the pH of the aqueous medium as appropriate, and it may comprise a supporting electrolyte. The aqueous medium may for instance comprise a redox couple, or a member of a redox couple which may be partially oxidised or reduced to provide the redox couple. The redox couple may chosen from those known in the art such as $Fe^{2+}/Fe^{3+}$, ferrocene/ferrocenium or $Ru^{2+}/Ru^{3+}$. Examples of such are ferro/ferricyanide, ruthenium hexamine and ferrocene carboxlic acid.

Alternatively, when one of the liquid and the fluid medium is polar, the polar medium may comprise a polar organic solvent. The polar organic solvent may for instance be a protic organic solvent, such as an alcohol, or it may be an aprotic polar organic solvent.

The liquid of the droplets may be any liquid suitable for performing experiments of the type described below. Different droplets may comprise different liquids.

Where the other of the liquid and the fluid medium is apolar, then the apolar medium may comprise an oil. The oil may be a single compound, or the oil may comprise a mixture of two or more compounds.

In one example, the oil is pure alkane hydrocarbon.

The oil may for instance comprise silicone oil. Suitable silicone oils include, for instance, poly(phenyl methyl siloxane) and poly(dimethylsiloxane) (PDMS). The silicone oil may comprise a hydroxy-terminated silicone oil, for instance hydroxy terminated PDMS.

Additionally or alternatively, the oil may comprise a hydrocarbon, for instance hexadecane, although any suitable hydrocarbon may be used. When the oil comprises a hydrocarbon it may comprise a single hydrocarbon compound, or a mixture of two or more hydrocarbons. When the oil comprises a hydrocarbon, the hydrocarbon may be branched or unbranched. The hydrocarbon may for instance be squalene, hexadecane or decane. In one embodiment it is hexadecane. However, in some embodiments the hydrocarbon may be substituted with a halogen atom, for instance bromine.

The oil may comprise a mixture of one or more silicone oils and one or more hydrocarbons. The silicone oil and hydrocarbon in the mixture may both be as further defined above. The silicone oil may for instance be poly(phenyl methyl siloxane) or PDMS.

Other types of oil are also possible. For example, the oil may be a fluorocarbon or a bromo-substituted $C_{10}$-$C_{30}$ alkane.

Amphipathic Molecules

In the case that one of the liquid and the fluid medium is polar, and the other of the liquid and the fluid medium being apolar, then the droplets may further comprise amphipathic molecules at the interface between the liquid of the droplets and the fluid medium. Such amphipathic molecules serve to stabilise the droplets in the fluid medium prior to formation of a droplet interface. Also, the amphipathic molecules may allow the droplet interface, when formed, to comprise a membrane of amphipathic molecules.

Numerous different types of amphipathic molecules may be used. Some non-limitative examples of types of amphipathic molecules that may be used are as follows.

In one example, the amphipathic molecules may comprise a lipid, which may have a single component or a mixture of components, as is conventional when forming lipid bilayers.

Any lipids that form a membrane such as a lipid bilayer may be used. The lipids are chosen such that a lipid bilayer having the required properties, such as surface charge, ability to support membrane proteins, packing density or mechanical properties, is formed. The lipids can comprise one or more different lipids. For instance, the lipids can contain up to 100 lipids. The lipids preferably contain 1 to 10 lipids. The lipids may comprise naturally-occurring lipids and/or artificial lipids.

The lipids can also be chemically-modified.

Amphipathic polymer membranes are preferred over lipid membranes due to their ability to withstand higher voltages.

In another example, the amphipathic molecules may comprise an amphipathic compound comprising a first outer hydrophilic group, a hydrophobic core group, and a second outer hydrophilic group, wherein each of the first and second outer hydrophilic groups is linked to the hydrophobic core group.

Some such amphipathic compounds are disclosed in WO 2014/064444.

Other such amphipathic compounds are disclosed in U.S. Pat. No. 6,916,488 which is incorporated herein by reference and discloses a number of polymeric materials that can be employed in the apparatus 1 as planar amphipathic membranes. In particular triblock copolymers are disclosed, for example silicon triblock copolymer membranes such as poly(2-methyloxazoline)-block-poly(dimethylsiloxane)-block-poly(2-methyloxazoline) (PMOXA-PDMS-PMOXA).

Examples of silicone triblock polymers that may be employed are 7-22-7 PMOXA-PDMS-PMOXA, 6-45-6 PMOXA-PE-PMOXA and 6-30-6 PMOXA-PDMS-PMOXA, where the nomenclature refers to the number of subunits.

Such triblock copolymers may be provided in vesicle form in the droplets.

Depending on the nature of the amphipathic molecules, the membranes may be bilayers of the amphipathic molecules or may be monolayers of the amphipathic molecules.

The amphipathic molecules may alternatively be replaced by another surfactant.

Different droplet interfaces may comprise membranes of different amphipathic molecules, for example membranes comprising a lipid bilayer and a polymer membrane such as a silicone triblock polymer membrane as described above, such as disclosed in WO2017/004504.

The electrical measurements that are taken may be used to study the membrane of amphipathic molecules itself, or interactions thereof, for example to study drug-membrane permittivity.

Transmembrane Pore

In general any transmembrane pore may be used that is capable of inserting into the droplet interface. Different droplets may comprise the same or different transmembrane pore, so that when plural droplet interfaces are formed between different plural droplet pairs, the same or different transmembrane pore may insert into those droplet interfaces.

Some non-limitative examples of types of transmembrane pore that may be used are as follows.

A transmembrane pore is a channel structure that provides a pathway from one of a membrane to the other through which ions may flow. The channel may vary in width along its length and typically has an inner diameter of between 0.5 nm and 10 nm.

Any suitable transmembrane pore may be used in the invention. The pore may be biological or artificial. Suitable pores include, but are not limited to, protein pores, polynucleotide pores and solid state pores. The pore may be a DNA origami pore (Langecker et al., Science, 2012; 338: 932-936). Suitable DNA origami pores are disclosed in WO2013/083983.

The transmembrane pore is preferably a transmembrane protein pore.

The transmembrane protein pore may be a monomer or an oligomer. The pore may be a hexameric, heptameric, octameric or nonameric pore. The pore may be a homo-oligomer or a hetero-oligomer.

The transmembrane protein pore imay be derived from CsgG, such as from CsgG from E. coli Str. K-12 substr. MC4100. Examples of suitable CsgG pores are described in WO-2016/034591, WO-2017/149316, WO-2017/149317 and WO-2017/149318.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore comprises amino acids that facilitate interaction with an analyte, such as a nucleotide, polynucleotide or nucleic acid. The pore may be modified by for example substitution or deletion of one of more amino acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as Mycobacterium smegmatis porin (Msp), for example MspA, MspB, MspC or MspD, CsgG, outer membrane porin F (OmpF), outer membrane porin G (OmpG), outer membrane phospholipase A and Neisseria autotransporter lipoprotein (NalP) and other pores, such as lysenin. α-helix bundle pores comprise a barrel or channel that is formed from α-helices. Suitable α-helix bundle pores include, but are not limited to, inner membrane proteins and a outer membrane proteins, such as WZA and ClyA toxin.

The transmembrane pore may be derived from or based on Msp, α-hemolysin (α-HL), lysenin, CsgG, ClyA, Sp1 and haemolytic protein fragaceatoxin C (FraC). The transmembrane protein pore is preferably derived from CsgG, more preferably from CsgG from E. coli Str. K-12 substr. MC4100.

The transmembrane pore may be derived from lysenin. Suitable pores derived from lysenin are disclosed in WO 2013/153359.

The pore may be a variant of the above listed nanopores. The variant may be at least 55%, at least 60%, at least 65%, at least 70%, at least 75%, at least 80%, at least 85%, at least 90% and more preferably at least 95%, 97% or 99% homologous based on amino acid similarity or identity to the amino acid sequence.

Standard methods in the art may be used to determine homology. For example the UWGCG Package provides the BESTFIT program which can be used to calculate homology, for example used on its default settings (Devereux et al (1984) Nucleic Acids Research 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/). Similarity can be measured using pairwise identity or by applying a scoring matrix such as BLOSUM62 and converting to an equivalent identity. Since they represent functional rather than evolved changes, deliberately mutated positions would be masked when determining homology. Similarity may be determined more sensitively by the application of position-specific scoring matrices using, for example, PSIBLAST on a comprehensive database of protein sequences. A different scoring matrix could be used that reflect amino acid chemico-physical properties rather than frequency of substitution over evolutionary time scales (e.g. charge).

Amino acid substitutions may be made to the amino acid sequence of SEQ ID NO: 3, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid.

Any of the proteins described herein, such as the transmembrane protein pores, may be made synthetically or by recombinant means. For example, the pore may be synthesised by in vitro translation and transcription (IVTT). The amino acid sequence of the pore may be modified to include non-naturally occurring amino acids or to increase the stability of the protein. When a protein is produced by synthetic means, such amino acids may be introduced during production. The pore may also be altered following either synthetic or recombinant production.

Any of the proteins described herein, such as the transmembrane protein pores, can be produced using standard methods known in the art. Polynucleotide sequences encoding a pore or construct may be derived and replicated using standard methods in the art. Polynucleotide sequences encoding a pore or construct may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The pore may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Analyte

The droplets may comprise an analyte that is capable of interaction with the transmembrane pore, also referred to as a target analyte, the template analyte or the analyte of interest. For example, the analyte may be a polymer or a drug.

Electrical measurements that are taken may be dependent on the interaction of the analyte with the transmembrane pore. The electrical measurements may be measurements of ion current through the pore.

Where the electrical measurements are dependent on the interaction of the analyte with the transmembrane pore, the analysis may determine the presence, absence or one or more characteristics of a target analyte. The analysis may determine the presence, absence or one or more characteristics of a target analyte. Where the analyte is a polymer comprising polymer units, in the analysis the electrical measurements may be processed to derive estimated identities of the polymer units, or to count polymer units or determine length of the polymer. Control experiments can be carried out in the presence of different analytes or polymer units, to determine how analytes affect the electrical measurements as the basis for the analysis.

The analysis may be performed using any suitable known technique, including techniques employing a Hidden Markov Model, for example as described in WO-2013/041878 or WO-2015/140535; techniques employing machine learning for example as described in Boza et al., "DeepNano: Deep recurrent neural networks for base calling in MinION nanopore reads", PLoS ONE 12(6): e0178751, 5 Jun. 2017; techniques employing comparison of feature vectors for example as described in WO-2013/121224; or any other suitable technique.

Such interaction may occur as an analyte moves with respect to, such as translocating through, the pore. In that case, the electrical measurements may be taken as the analyte moves with respect to the pore. Such movement may occur while a potential difference is applied between the droplets, i.e. across the pore. The applied potential typically results in the formation of a complex between the pore and a polynucleotide binding protein. The applied potential difference may be a voltage potential. Alternatively, the applied potential difference may be a chemical potential. An example of this is using a salt gradient across an amphiphilic layer. A salt gradient is disclosed in Holden et al., J Am Chem Soc. 2007 Jul. 11; 129(27):8650-5.

The target analyte may be a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive or an environmental pollutant.

The analyte may be an amino acid, a peptide, a polypeptides and/or a protein. The amino acid, peptide, polypeptide or protein can be naturally-occurring or non-naturally-occurring. The polypeptide or protein can include within them synthetic or modified amino acids. A number of different types of modification to amino acids are known in the art. Suitable amino acids and modifications thereof are above. For the purposes of the invention, it is to be understood that the target analyte can be modified by any method available in the art.

The analyte protein can be an enzyme, an antibody, a hormone, a growth factor or a growth regulatory protein, such as a cytokine. The cytokine may be selected from interleukins, preferably IFN-1, IL-1, IL-2, IL-4, IL-5, IL-6, IL-10, IL-12 and IL-13, interferons, preferably IL-γ, and other cytokines such as TNF-α. The protein may be a bacterial protein, a fungal protein, a virus protein or a parasite-derived protein.

The target analyte may be a nucleotide, an oligonucleotide or a polynucleotide. Nucleotides and polynucleotides are discussed below. Oligonucleotides are short nucleotide polymers which typically have 50 or fewer nucleotides, such 40 or fewer, 30 or fewer, 20 or fewer, 10 or fewer or 5 or fewer nucleotides. The oligonucleotides may comprise any of the nucleotides discussed below, including the abasic, and modified, nucleotides.

At least a portion of the polynucleotide may be double stranded.

The polynucleotide can be a nucleic acid, such as deoxyribonucleic acid (DNA) or ribonucleic acid (RNA). The polynucleotide can comprise one strand of RNA hybridised to one strand of DNA.

The polynucleotide can be any length. For example, the polynucleotide can be at least 10, at least 50, at least 100, at least 500 nucleotides or nucleotide pairs in length. The polynucleotide can be 1000 or more, 10000 or more, 100000 or more, or 1000000 or more nucleotides or nucleotide pairs in length.

Any number of polynucleotides can be investigated. For instance, the method of the invention may concern characterising 2, 3, 4, 5, 6, 7, 8, 9, 10, 20, 30, 50, 100 or more polynucleotides. If two or more polynucleotides are characterised, they may be different polynucleotides or two instances of the same polynucleotide.

The polynucleotide can be naturally occurring or artificial.

Where the analyte is a polynucleotide comprising nucleotides and estimated identities of the polymer units are derived from the electrical measurements, then strand characterisation/sequencing or exonuclease characterisation/sequencing may be applied.

In strand sequencing, the polynucleotide may be translocated through the nanopore either with or against an applied potential. In this case, the electrical measurements are indicative of one or more characteristics of multiple nucleotides.

The droplets may contain a polymer binding moiety such as an enzyme to control translocation of the polymer through the pore. The moiety can be a molecular motor using for example, in the case where the moiety is an enzyme, enzymatic activity, or as a molecular brake.

Where the polymer is a polynucleotide there are a number of methods proposed for controlling the rate of translocation including use of polynucleotide binding enzymes. Suitable enzymes for controlling the rate of translocation of polynucleotides include, but are not limited to, polymerases, helicases, exonucleases, single stranded and double stranded binding proteins, and topoisomerases, such as gyrases. For other polymer types, moieties that interact with that polymer type can be used. The polymer interacting moiety may be any disclosed in WO-2010/086603, WO-2012/107778, and Lieberman K R et al, J Am Chem Soc. 2010; 132(50):17961-72), and for voltage gated schemes (Luan B et al., Phys Rev Lett. 2010; 104(23):238103).

The polymer binding moiety can be used in a number of ways to control the polymer motion. The moiety can move the polymer through the nanopore with or against the applied field. The moiety can be used as a molecular motor using for example, in the case where the moiety is an enzyme, enzymatic activity, or as a molecular brake. The translocation of the polymer may be controlled by a molecular ratchet that controls the movement of the polymer through the pore. The molecular ratchet may be a polymer binding protein. For polynucleotides, the polynucleotide binding protein is preferably a polynucleotide handling enzyme.

Preferred polynucleotide handling enzymes are polymerases, exonucleases, helicases and topoisomerases, such as gyrases. A polynucleotide handling enzyme may be for example one of the types of polynucleotide handling enzyme described in WO-2015/140535 or WO-2010/086603.

In an embodiment, one or more of the membranes may be a selective membrane having multiple pores inserted to provide a kind of frit alternative to supply a reagent. This embodiment may be employed for example in a three pore system comprising a droplet pair and a third droplet connected to a droplet of the pair, whereby the interface between the third droplet and the droplet of the pair comprises multiple pores. The third droplet may for example comprise an electrochemical mediator such as ferricyanide $[Fe(CN)_6]^{3-/2-}$.

Different droplet interfaces may have different transmembrane pores inserted thereon.

Coupling

The analyte may contain an anchor to couple it to a membrane, or a tether to couple it to a pore. The membrane may be functionalised to facilitate coupling of an analyte. The pore may be modified to facilitate tethering of the analyte. Methods of coupling an analyte to a membrane that are known in the art may be used, for example as described in WO-2012/164270 or WO-2015/150786. Methods of tethering an analyte to a pore that are known in the art may be used, for example as described in WO-2012/164270 or PCT/GB2017/053603.

Sample

Droplets 1 may be prepared from a sample. Such a sample may be known to contain or suspected to contain an analyte The sample may be a biological sample. The sample may be obtained from or extracted from any organism or microorganism.

The sample may be obtained from or extracted from any virus.

The sample is preferably a fluid sample. The sample typically comprises a body fluid of the patient. The sample may be urine, lymph, saliva, mucus or amniotic fluid but is preferably blood, plasma or serum.

The sample may be human in origin, but alternatively it may be from another mammal animal such as from commercially farmed animals such as horses, cattle, sheep, fish, chickens or pigs or may alternatively be pets such as cats or dogs. Alternatively, the sample may be of plant origin, such as a sample obtained from a commercial crop, such as a cereal, legume, fruit or vegetable.

The sample may be or derived from a non-biological sample. The non-biological sample is preferably a fluid sample. Examples of non-biological samples include surgical fluids, water such as drinking water, sea water or river water, and reagents for laboratory tests.

Example

An Example of use of the apparatus 1 which has been carried out is as follows.

The apparatus 1 of the Example was designed to perform DNA sample preparation and sequencing in one, portable platform. The key sequencing element is a protein nanopore embedded in a polymer membrane that is formed at the droplet interface 2 between two aqueous droplets 1 in an AM-EWOD device 34 of the type described above.

In this Example, the liquid of the droplets 1 was aqueous solution, the droplets contained amphipathic molecules that were triblock copolymers of the type describe above in vesicle form, and the fluid medium 50 was pure alkane hydrocarbon.

Figure 17A:
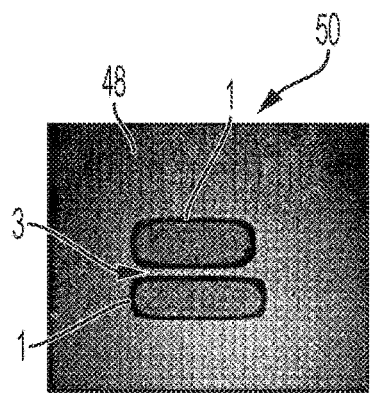
FIG. 17 is two images of an array of actuation electrodes in the AM-EWOD device.
Figure 17B:
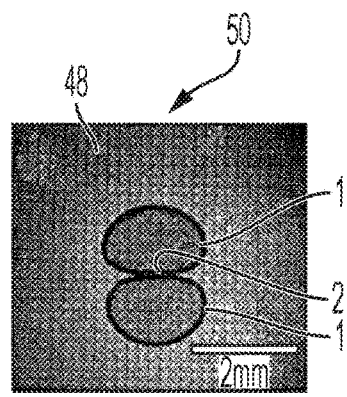

The Example used an AM-EWOD device 31 having an array 50 of actuation electrodes 48 as shown in FIG. 17 which are images also showing two droplets 1. FIG. 17a was taken at the end of the first stage of the method described above with the droplets 1 in the energised state in proximity with the gap 3 therebetween. FIG. 17b was taken after the end of the second stage when the droplets 1 have relaxed to form a droplet interface 2. Each actuation electrode 48 in the array was of dimensions 200×200 µm and thus much smaller than any droplet 1 used.

Figure 18:
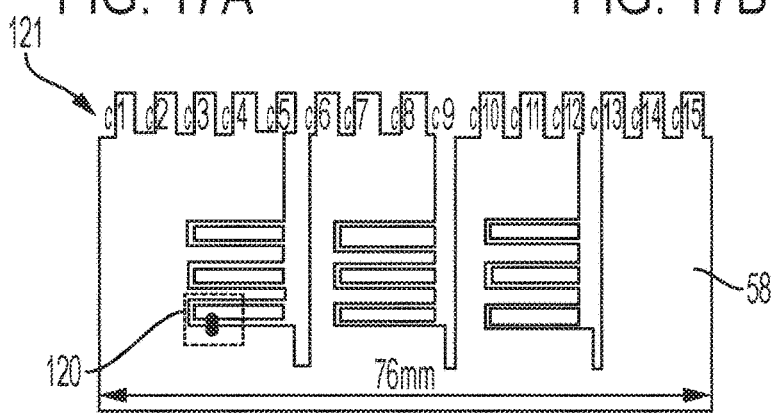
FIG. 18 is a diagram of a patterned layer of conductive material in the AM-EWOD device.

In the AM-EWOD device 31, the layer 58 of conductive material is patterned as shown in FIG. 18, wherein the box 120 shows the region where the images of FIG. 17 were taken. FIG. 18 shows contact pads 121 labelled C1 through C15 at the top edge. A sensor electrode 100 connected to the contact pads 121 labelled C2 (grounded) and a sensor electrode 100 connected to the contact pads 121 labelled C5 (recording) were used for electrical recording from droplet interface 2 in panel FIG. 17*b*.

Recording electrodes were integrated into the AM-EWOD device 31 to facilitate voltage application and the current recording that comprises the pore DNA sequencing signal.

In the Example, current recording was performed on individual droplet interfaces 2 using a standard patch clamp amplifier. For multichannel recording from an array of droplet interfaces 2 in parallel, a multichannel recording system can be employed. To enable recording of sufficient quality for DNA sequencing (<1 pA rms @ 5 KHz), the system must be virtually free of electrical noise. Therefore, preferentially, the apparatus 1 operates in two mutually exclusive modes, referred to as an EWOD mode and a recording mode.

In the EWOD mode, all features in the layer 58 of conductive material are connected to the control electronics 38 which supplies a part of the voltage necessary for movement. Because EWOD uses high frequency, large AC voltage fields, recording cannot take place while the EWOD field is on. Specifically, the EWOD field generates noise that obscures the DNA signal. Therefore, once the droplets 1 are positioned as desired, the control electronics 38 is unplugged, although internal switching components could alternatively be used. Once EWOD is unplugged, multipole switches are actuated The entire apparatus 1 was enclosed in a Faraday cage during recording to prevent interference from ambient noise. Thus, during recording mode, the droplets are not held in place by any electrically induced forces.

Figure 19:
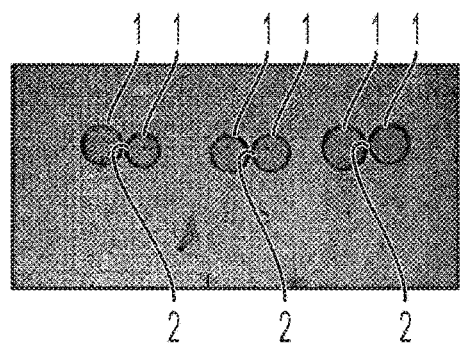
FIG. 19 is an image of an array of actuation electrodes in the AM-EWOD device on which three systems of two droplets are formed.

Using the method described above, the AM-EWOD device 34 was used to create three systems each consisting of two droplets 1 having a droplet interfaces 2 therebetween, as shown in FIG. 19.

Formation of droplet interfaces 2 was performed as follows.

Simply bringing manipulating two droplets 1 to bring them together under the application of actuation signals to the actuation electrodes 48 was possible, but challenging because the droplets 1 tended to fuse.

Figure 20:
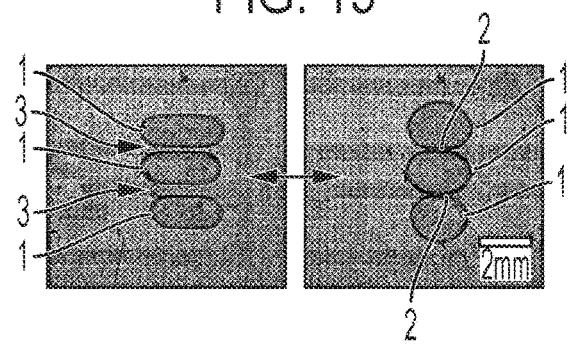
FIG. 20 is images of two sets of three droplets before and after formation of two droplet interfaces therebetween.

Instead, the method described above was used. Specifically, in the first stage, droplets 1 were energised into rectangular shapes with an aspect ratio greater than 1.5. The long edges of these shapes were brought into 1-2 pixel proximity and centered. An example of this stage applied to three droplets 1 is shown in FIG. 20, left hand side.

In the second stage, the actuation signals were switched. The droplets naturally relaxed back into relaxed circular shapes to reduce their surface area to volume ratio. Relaxation causes the surfaces of the droplets facing each other across the gaps 3 to contact and form a droplet interface 2 (which may be referred to as passive formation). Using this approach, DIBs may be created between two or more droplets. An example of this stage applied to three droplets 1 is shown in FIG. 20, right hand side.

Such formation of droplet interfaces 2 was a reversible process.

Although the control electronics 38 produced noise that would obscure the DNA sequencing signal, it is still possible to observe a large current event, such as pore insertion into the droplet interface 2. As a demonstration, the apparatus 1 was set up such that the AM-EWOD device 34 could be powered to a low noise mode and droplets were positioned to form a droplet interface while recording electrical current.

Figure 21:
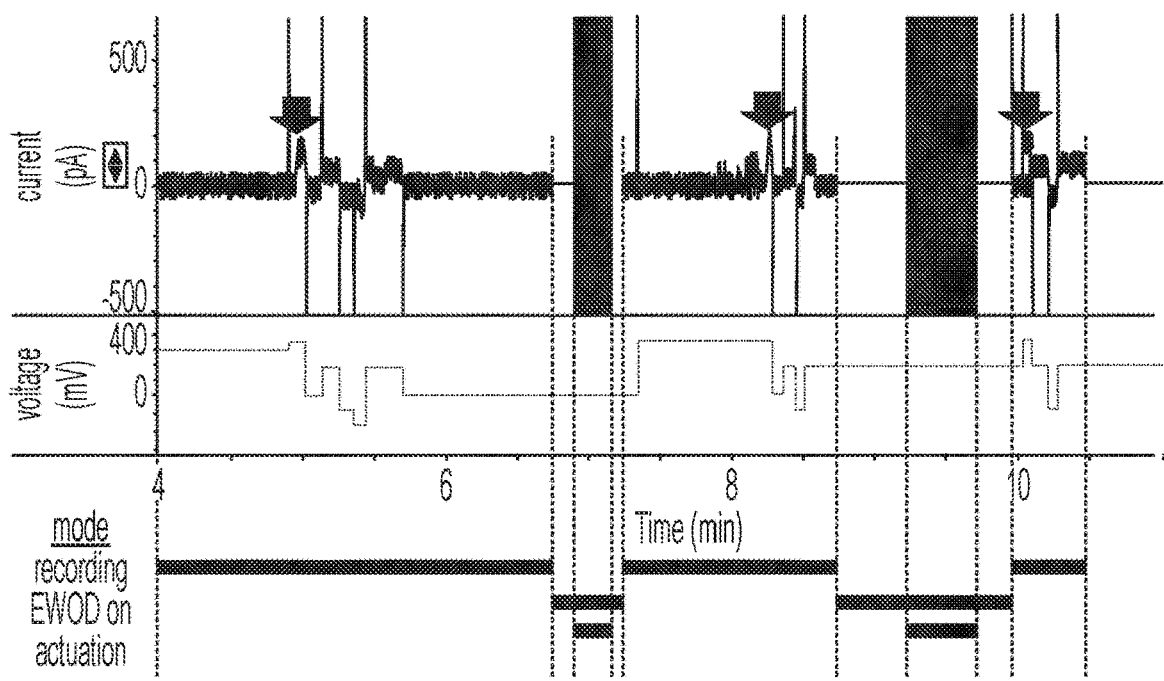
FIG. 21 is a plot of electrical measurements of current and voltage during formation, separation and re-formation of droplet interfaces in the AM-EWOD device.

FIG. 21 shows the electrical current thus recorded. Within this signal it is possible to observe formation of droplet interfaces 2, unzipping, reformation and pore insertion. Multiple cycles of pore insertion and membrane disconnect and reconnect are shown. Thick black arrows denote pore insertion. The recording time bars indicate recording mode, the EWODon time bars represent EWOD mode and the actuation time bars indicate droplet actuation and shaping. Off-scale noise is observed during droplet actuation.

Pore insertion was observed as a jump in current from 0 to ~200 pA at 300 mV. After pore insertion, voltage was switched to zero and the system switched to EWOD mode. Droplets 1 were separated, and then a droplet interface was reformed. Note that during this time, the noise goes beyond the scale of the current recording instrument.

The system was then switched back to recording mode and a voltage of 300 mV applied. After observing another pore insertion, the cycle was repeated once more for a total of three pore insertions and two separations of droplet interfaces 2. This demonstrates the ability to form droplet interfaces 2, insert pores, separate droplets 1 and reform droplet interfaces 2 repeatedly in the AM-EWOD device 34.

DNA detection and sequencing was performed as follows.

By placing the amphipathic molecules in the droplets 1 rather than the fluid medium 50, it becomes possible to make asymmetric membranes. For example, the DNA droplet could have a lower concentration of polymer vesicle relative to the opposing droplet or it could have an entirely different polymer composition. This may provide flexibility in optimizing sample prep, DIB formation, pore insertion, DNA sequencing or further processes.

Figure 22:
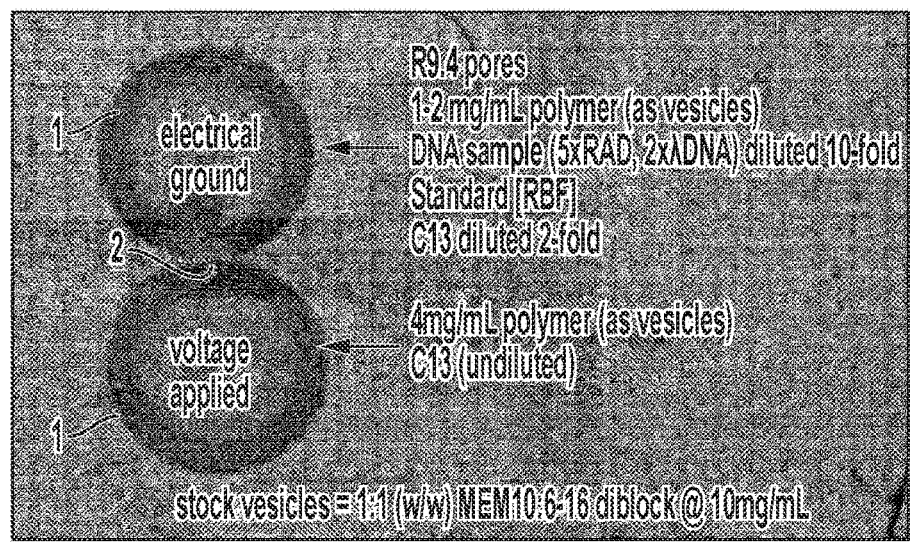
FIG. 22 is an image of a system of two droplets in the AM-EWOD device.

In one example, an asymmetric pair of droplets 1 was used as shown in FIG. 22 to detect short DNA strands (adapter). FIG. 22 shows an example of droplet interface 2 comprising a membrane of amphipathic molecules having a concentration below 2 mg/mL in the DNA droplet (top) to aids pore insertion. Higher polymer concentration in the opposing droplet (bottom) aids stability.

Figure 23:
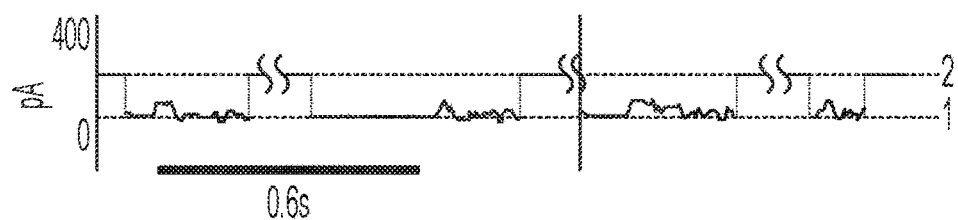
FIG. 23 is a trace of a current signal obtained in the system of droplets in FIG. 22.

FIG. 23 shows an example of the characteristic adapter signal obtained from the droplet interface in FIG. 22. Current levels, shown in pA, represent the open pore (2) and an adapter-occupied pore. In FIG. 23, the characteristic squiggle of the adapter blockade is an easily recognizable signal that established the quality of the pore and overall system configuration.

The same approach can be applied to obtain sequencing signals from single strands of DNA. A droplet interface 2 was created from a droplet 1 containing a 3.6 Kb single-strand DNA sample, sequencing reagents and enzymes, polymer vesicles, mediator buffer and nanopores. The opposing droplet 1 contained vesicles of amphipathic molecules and mediator+ salts to osmotically balance with the DNA droplet 1.

After observing a single pore insertion, the control electronics 38 were unplugged and electrodes switched to recording mode. During sequencing, a strand of DNA threads into the pore which is then pulled through by the applied voltage. The speed of threading is regulated by an attached enzyme that is, in turn, powered by ATP turnover in the droplet.

Figure 24:
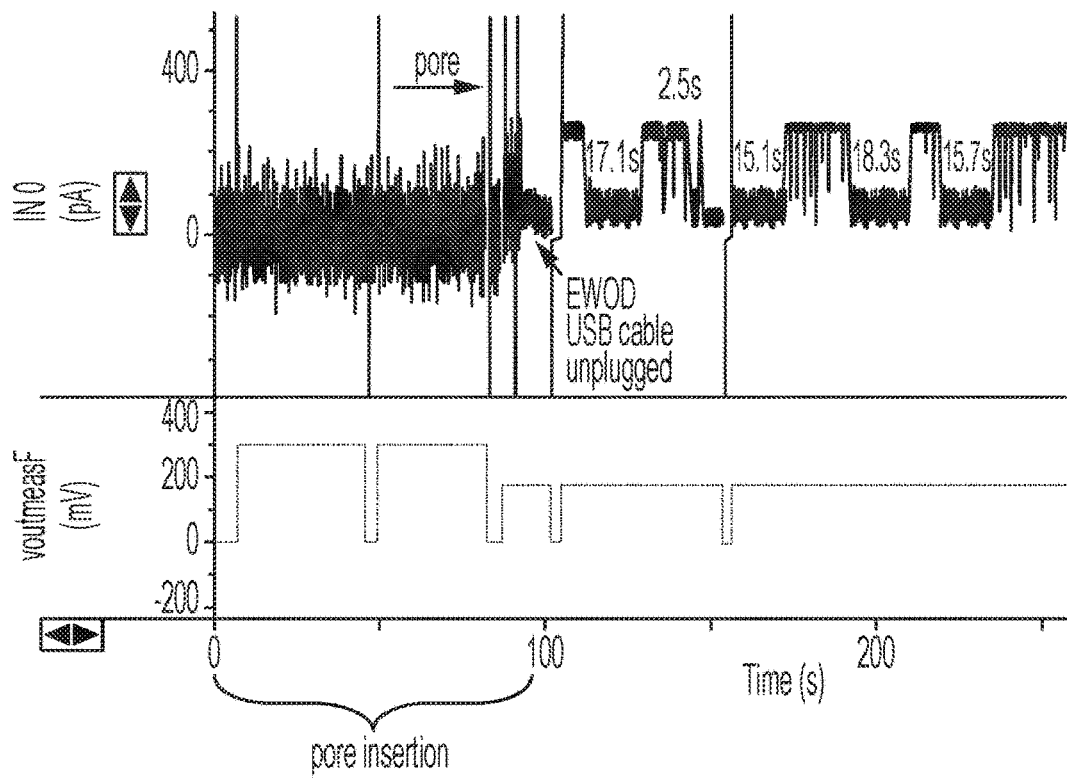
FIG. 24 is a plot of electrical measurements of current and voltage during an experiment in which DNA translocates through a pore in a system of two droplets in the AM-EWOD device.

The DNA used in this experiment was a standard 3.6 Kb long with a known sequence, so each stand was expected to thread through the pore for a similar amount of time. FIG. 24 shows an example of the electrical measurements taken, showing DNA threading events at 180 mV. Note that the current blockades last from 15.1 to 18.3 seconds, which correlates to roughly 200 bases per second. This is the translocation speed expected for a nanopore operating under the conditions of the experiment. Since each DNA strand in the control sample is identical, the squiggle sequence from each translocation event should be the same.

Figure 25:
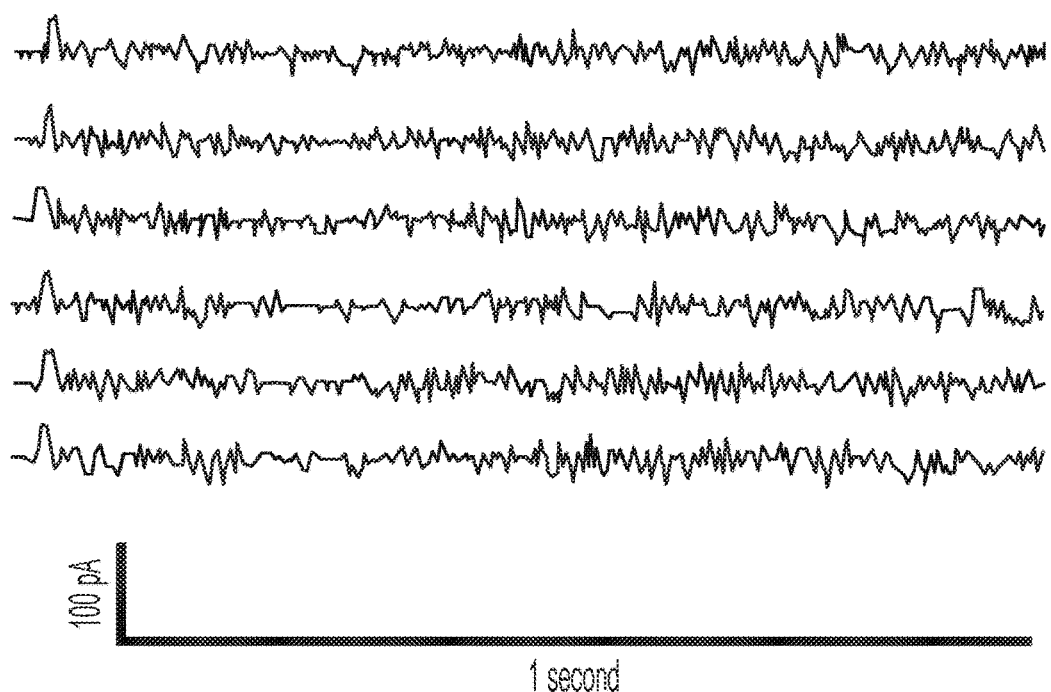
FIG. 25 is a plot of electrical measurements of current for six translocation events.

FIG. 25 is a plot of expanded current traces for six translocation events, each showing a characteristic "a-basic" peak followed by the sequencing signal. Note that all traces possess the same profile. A rough alignment of these current traces of six translocation events shows that the signal pattern is the same for each strand of DNA.

The invention claimed is:

1. An electro-wetting device for taking measurements across a droplet interface, the electro-wetting device comprising:
   a first substrate supporting an array of actuation electrodes;
   an insulator layer covering the actuation electrodes and having a hydrophobic surface,
   a second substrate facing the hydrophobic surface of the insulator layer and supporting at least one set of at least two sensor electrodes, wherein the second substrate is coated by a hydrophobic material forming a further hydrophobic surface facing the hydrophobic surface of the insulator layer, the electro-wetting device being arranged to receive the fluid medium and the droplets disposed on the further hydrophobic surface of the hydrophobic material coating the second substrate, as well as the hydrophobic surface of the insulator layer, wherein the hydrophobic material coating the second substrate has apertures exposing at least part of the sensor electrodes,
   the electro-wetting device being arranged to receive a fluid medium and droplets comprising liquid in the fluid medium disposed on the hydrophobic surface, the actuation electrodes being configured to receive actuation signals for electro-wetting and moving received droplets in order to form at least one system of droplets having one or more droplet interfaces between droplets, and the sensor electrodes of each set being configured to make electrical connections to respective droplets in the at least one system of droplets.

2. An electro-wetting device according to claim 1, further comprising a control system connected to the actuation electrodes and configured to apply actuation signals to the actuation electrodes for manipulating received droplets.

3. An electro-wetting device according to claim 2, wherein the control system is configured to apply actuation signals to the actuation electrodes to form the at least one system of droplets aligned with the at least one set sensor electrodes.

4. An electro-wetting device according to claim 2, wherein the control system is arranged, while applying actuation signals to the actuation electrodes, to apply a reference signal to the sensor electrodes.

5. An electro-wetting device according to claim 2, wherein the control system is configured to apply actuation signals to the actuation electrodes selected to form a droplet interface at the interface between two droplets.

6. An electro-wetting device according to claim 1, wherein the second substrate further supports at least one further electrode, wherein the control system is connected to the further electrode and is arranged, while applying actuation signals to the actuation electrodes, to apply a reference signal to the further electrode.

7. An electro-wetting device according to claim 6, wherein the further electrode is deposited on a surface of the second substrate facing the first substrate.

8. An electro-wetting device according to claim 7, wherein the further electrode extends around the sensor electrodes.

9. An electro-wetting device according to claim 1, further comprising a sensor system connected to the sensor electrodes and configured to take electrical measurements between sensor electrodes that are electrically connected to respective droplets forming a droplet interface therebetween.

10. An electro-wetting device according to claim 9, wherein the electrical measurements include impedance measurements.

11. An electro-wetting device according to claim 9, wherein the sensor system is configured to take electrical measurements in a frequency range from a lower limit to an upper limit, wherein the lower limit is 1 Hz, 10 Hz or 100 Hz and the upper limit is 10 MHz, 100 KHz or 10 KHz, in any combination.

12. An electro-wetting device according to claim 1, wherein the sensor system is configured to take electrical measurements between respective sensor electrodes that make contact between respective droplets across a droplet interface comprising a membrane of amphipathic molecules having a transmembrane pore inserted therein.

13. An electro-wetting according to claim 12, wherein the electrical measurements are measurements of ion flow between droplets through a transmembrane pore.

14. An electro-wetting device according to claim 12, wherein the sensor system is arranged to take the electrical measurements while applying a potential difference between a respective pair of sensor electrodes.

15. An electro-wetting device according to claim 12, wherein the sensor system is arranged to take electrical measurements that are dependent on an analyte that interacts with the transmembrane pore.

16. An electro-wetting device according to claim 15, wherein the sensor system further comprises an analysis system configured to process the electrical measurements to analyse the analyte.

17. An electro-wetting device according to claim 12, wherein the analyte is a polymer comprising polymer units and the analysis system is configured to process the electrical measurements to derive estimated identities of the polymer units of the polymer.

18. An electro-wetting device according to claim 1, wherein the second substrate supports plural sets of at least two sensor electrodes.

19. An electro-wetting device according to claim 1, wherein the insulator layer comprises a layer of electrically insulating material coated by a hydrophobic material that forms said hydrophobic surface.

20. An electro-wetting device according to claim 1, wherein the sensor electrodes are deposited on a surface of the second substrate facing the first substrate.

21. An electro-wetting device according to claim 20, further comprising conductive tracks deposited on said surface of the second substrate inside the cell and connected to the sensor electrodes for providing electrical connection to a sensor system.

22. An electro-wetting device according to claim 1, wherein the second substrate further supports at least one further electrode.

23. An electro-wetting device according to claim 22, wherein the further electrode is deposited on a surface of the second substrate facing the first substrate.

24. An electro-wetting device according to claim 22, wherein the further electrode extends around the sensor electrodes.

25. An electro-wetting device according to claim 1, further comprising the fluid medium and two droplets comprising liquid in the fluid medium, received in the electro-wetting device.

26. An electro-wetting device according to claim 25, wherein one of the liquid and the fluid medium is polar, and the other of the liquid and the fluid medium is apolar, the droplets further comprising amphipathic molecules at the interface between the liquid of the droplets and the fluid medium, and the droplet interfaces comprise a membrane of amphipathic molecules.

27. An electro-wetting device according to claim 26, wherein the liquid is polar, and the fluid medium is apolar.

28. An electro-wetting device according to claim 25, wherein the fluid medium is a liquid medium.

29. An electro-wetting device according to claim 25, wherein at least one of the droplets comprises a transmembrane pore that is capable of insertion into the membrane of amphipathic molecules.

30. An electro-wetting device according to claim 29, wherein at least one of the droplets comprises an analyte that is capable of interaction with the transmembrane pore.

* * * * *

UNITED STATES PATENT AND TRADEMARK OFFICE
CERTIFICATE OF CORRECTION

| | |
|---|---|
| PATENT NO. | : 11,534,763 B2 |
| APPLICATION NO. | : 16/955762 |
| DATED | : December 27, 2022 |
| INVENTOR(S) | : Matthew Holden et al. |

It is certified that error appears in the above-identified patent and that said Letters Patent is hereby corrected as shown below:

On the Title Page

Item (30) should read:
(30) Foreign Application Priority Data
Dec. 21, 2017 (GB) .............................. 1721649.0

In the Specification

At Column 1, Line 3, immediately after the title, should read:
RELATED APPLICATIONS
This Application is a national stage filing under 35 U.S.C. § 371 of international application number PCT/US2018/067219, filed December 21, 2018, which claims the benefit of United Kingdom application number 1721649.0, filed December 21, 2017, each of which is herein incorporated by reference in its entirety.

In the Claims

At Column 33, Claim 1, Line 23, please replace "surf ace" with --surface--

At Column 33, Claim 1, Line 28, please replace "surf ace" with --surface--

At Column 33, Claim 1, Line 33, please replace "surf ace" with --surface--

Signed and Sealed this
Twenty-eighth Day of February, 2023

Katherine Kelly Vidal
*Director of the United States Patent and Trademark Office*